(12) United States Patent
O'Dea et al.

(10) Patent No.: US 9,555,014 B2
(45) Date of Patent: Jan. 31, 2017

(54) THERAPEUTIC REGIMENS

(71) Applicant: Radius Health, Inc.

(72) Inventors: Louis O'Dea, Hingham, MA (US); C. Richard Lyttle, Bala Cynwyd, PA (US); Jonathan Guerriero, Braintree, MA (US)

(73) Assignee: Radius Health, Inc., Waltham, MA (US)

( * ) Notice: Subject to any disclaimer, the term of this patent is extended or adjusted under 35 U.S.C. 154(b) by 0 days.

(21) Appl. No.: 14/281,475

(22) Filed: May 19, 2014

(65) Prior Publication Data

US 2016/0022608 A1    Jan. 28, 2016

Related U.S. Application Data

(63) Continuation of application No. 13/697,230, filed as application No. PCT/US2011/036311 on May 12, 2011, now abandoned.

(60) Provisional application No. 61/334,095, filed on May 12, 2010.

(51) Int. Cl.
*A61K 31/135* (2006.01)
*A01N 33/02* (2006.01)
*A61K 31/137* (2006.01)
*A61K 9/48* (2006.01)

(52) U.S. Cl.
CPC ............. *A61K 31/137* (2013.01); *A61K 9/485* (2013.01); *A61K 9/4866* (2013.01)

(58) Field of Classification Search
CPC .... A61K 31/137; C07C 217/84; C07C 217/86
USPC .......... 514/546, 647, 648, 649, 650
See application file for complete search history.

(56) References Cited

U.S. PATENT DOCUMENTS

| | | | |
|---|---|---|---|
| 5,411,981 A | 5/1995 | Gaillard-Kelly | |
| 5,695,955 A | 12/1997 | Krstenansky | |
| 5,723,577 A | 3/1998 | Dong | |
| 5,955,574 A | 9/1999 | Dong | |
| 5,969,095 A | 10/1999 | Dong | |
| 6,156,899 A | 12/2000 | Galey | |
| 6,159,959 A | 12/2000 | Miller | |
| 6,526,316 B2 | 2/2003 | Iga | |
| 6,544,949 B1 | 4/2003 | Dong | |
| 6,921,750 B2 | 7/2005 | Dong | |
| 6,960,474 B2 | 11/2005 | Salvati | |
| 7,097,631 B2 | 8/2006 | Trautman | |
| 7,186,683 B2 | 3/2007 | Henriksen | |
| 7,214,381 B2 | 5/2007 | Carrara | |
| 7,335,377 B2 | 2/2008 | Stern | |
| 7,363,075 B2 | 4/2008 | Stern | |
| 7,383,084 B2 | 6/2008 | Stern | |
| 7,410,948 B2 | 8/2008 | Dong | |
| 7,446,110 B2 | 11/2008 | Kaufman | |
| 7,537,795 B2 | 5/2009 | Cormier | |
| 7,556,821 B2 | 7/2009 | Ameri | |
| 7,558,625 B2 | 7/2009 | Levin | |
| 7,579,013 B2 | 8/2009 | Ameri | |
| 7,612,114 B2 | 11/2009 | Hamaoka | |
| 7,662,404 B2 | 2/2010 | Stern | |
| 7,803,770 B2 | 9/2010 | Dey | |
| 7,960,412 B2 | 6/2011 | Hamaoka | |
| 7,968,580 B2 | 6/2011 | Lanter | |
| 8,041,421 B2 | 10/2011 | Birchall | |
| 8,067,448 B2 | 11/2011 | Miller | |
| 8,133,505 B2 | 3/2012 | Stern | |
| 8,148,333 B2 | 4/2012 | Dey | |
| 8,268,872 B2 | 9/2012 | Miller | |
| 8,399,520 B2 | 3/2013 | Hamaoka et al. | |
| 8,455,525 B2 | 6/2013 | Miller | |
| 8,629,167 B2 | 1/2014 | Miller | |
| 8,642,632 B2 | 2/2014 | Miller | |
| 8,933,130 B2 * | 1/2015 | Lyttle ................. | A61K 31/136 514/579 |
| 8,987,319 B2 | 3/2015 | Miller | |
| 2003/0065008 A1 | 4/2003 | Labrie | |
| 2003/0135150 A1 | 7/2003 | Kuribayashi | |
| 2003/0143276 A1 | 7/2003 | Hsia | |
| 2003/0166836 A1 | 9/2003 | Dong | |
| 2004/0210080 A1 | 10/2004 | Meng | |
| 2005/0096586 A1 | 5/2005 | Trautman | |
| 2005/0106209 A1 | 5/2005 | Ameri | |
| 2005/0182105 A1 | 8/2005 | Nirschl | |
| 2005/0250749 A1 | 11/2005 | Labrie | |
| 2005/0261303 A1 | 11/2005 | Taniguchi | |
| 2005/0282749 A1 | 12/2005 | Henriksen | |
| 2006/0106067 A1 | 5/2006 | Shiraishi | |
| 2006/0116364 A1 | 6/2006 | Hamaoka | |
| 2006/0116415 A1 | 6/2006 | Sui et al. | |

(Continued)

FOREIGN PATENT DOCUMENTS

| | | |
|---|---|---|
| EP | 0 916 652 A1 | 5/1999 |
| EP | 0 580 459 B1 | 3/2001 |
| EP | 1 911 743 A1 | 4/2008 |
| EP | 2366401 A1 | 9/2011 |
| GB | 1547758 A | 6/1979 |
| JP | 6016957 A | 1/1985 |
| JP | 01261381 A | 10/1989 |
| WO | WO 94/27989 A1 | 12/1994 |
| WO | WO 96/35447 A1 | 11/1996 |
| WO | WO 96/41793 A1 | 12/1996 |

(Continued)

OTHER PUBLICATIONS

Arun, B., et al., "The search for the ideal SERM," Expert Opin. Pharmacother., 3(6): 681-691 (2002).

(Continued)

*Primary Examiner* — My-Chau T Tran
(74) *Attorney, Agent, or Firm* — Perkins Coie LLP; Yingli Wang

(57) ABSTRACT

This invention relates to clinically useful therapeutic regimens comprising the administration of (R)-6-(2-(ethyl(4-(2-(ethylamino)ethyl)benzyl)amino)-4-methoxyphenyl)-5,6,7,8-tetrahydronaphthalen-2-ol.

36 Claims, 2 Drawing Sheets

(56) References Cited

U.S. PATENT DOCUMENTS

| | | |
|---|---|---|
| 2006/0142387 A1 | 6/2006 | Cadilla |
| 2006/0148893 A1 | 7/2006 | Blanc |
| 2006/0211756 A1 | 9/2006 | Zhang |
| 2006/0287327 A1 | 12/2006 | Labrie |
| 2007/0088039 A1 | 4/2007 | Balog |
| 2007/0155664 A1 | 7/2007 | Ranklove |
| 2007/0184096 A1 | 8/2007 | Ameri |
| 2007/0254875 A1 | 11/2007 | Zhi |
| 2007/0281906 A1 | 12/2007 | Dalton |
| 2007/0287949 A1 | 12/2007 | Levin |
| 2007/0299009 A1 | 12/2007 | Dong |
| 2008/0039775 A1 | 2/2008 | Ameri |
| 2008/0057068 A1 | 3/2008 | Dalton |
| 2008/0114048 A1 | 5/2008 | Sui |
| 2008/0119401 A1 | 5/2008 | Dong |
| 2009/0042866 A1 | 2/2009 | Lennox |
| 2009/0042967 A1 | 2/2009 | Hasuoka |
| 2009/0117158 A1 | 5/2009 | Ameri |
| 2009/0198189 A1 | 8/2009 | Simons |
| 2009/0253758 A1 | 10/2009 | Miller |
| 2009/0264534 A1 | 10/2009 | Dalton |
| 2009/0325930 A1 | 12/2009 | Hamaoka |
| 2010/0041721 A1 | 2/2010 | Miller |
| 2010/0105733 A1 | 4/2010 | Lyttle |
| 2010/0119568 A1 | 5/2010 | Ameri |
| 2010/0152236 A1 | 6/2010 | Yamamoto |
| 2010/0152649 A1 | 6/2010 | Ameri |
| 2010/0160895 A1 | 6/2010 | Ameri |
| 2010/0221305 A1 | 9/2010 | Ameri |
| 2010/0226966 A1 | 9/2010 | Daddona |
| 2011/0092425 A1 | 4/2011 | Dey |
| 2011/0124617 A1 | 5/2011 | Lyttle et al. |
| 2011/0172609 A1 | 7/2011 | Moga |
| 2011/0224267 A1 | 9/2011 | Miller |
| 2011/0288485 A1 | 11/2011 | Tokumoto |
| 2012/0004270 A1 | 1/2012 | Miller |
| 2013/0006217 A1 | 1/2013 | Hattersley |
| 2013/0041007 A1 | 2/2013 | Miller |
| 2013/0053448 A1 | 2/2013 | O'Dea et al. |
| 2013/0085105 A1 | 4/2013 | Deasy |
| 2013/0116288 A1 | 5/2013 | Miller |
| 2013/0157955 A1 | 6/2013 | Dey |
| 2014/0046292 A1 | 2/2014 | Hattersley |
| 2014/0046293 A1 | 2/2014 | Hattersley |
| 2014/0343499 A1 | 11/2014 | Zhang |

FOREIGN PATENT DOCUMENTS

| | | | |
|---|---|---|---|
| WO | WO 97/02834 A1 | 1/1997 | |
| WO | WO 97/49709 A1 | 12/1997 | |
| WO | WO 98/30590 A3 | 7/1998 | |
| WO | WO 01/36039 A2 | 5/2001 | |
| WO | 01/49673 A2 | 7/2001 | |
| WO | WO 01/49673 A2 | 7/2001 | |
| WO | WO 02/16310 A1 | 2/2002 | |
| WO | WO 03/011824 A1 | 2/2003 | |
| WO | 03/63859 A1 | 8/2003 | |
| WO | WO 03/063859 A1 | 8/2003 | |
| WO | WO 03/068217 A1 | 8/2003 | |
| WO | 03/091239 A1 | 11/2003 | |
| WO | WO 03/091239 A1 | 11/2003 | |
| WO | WO 03/096980 A2 | 11/2003 | |
| WO | 03/099292 A1 | 12/2003 | |
| WO | WO 03/099292 A1 | 12/2003 | |
| WO | WO 03/105772 | 12/2003 | |
| WO | WO 2004/041277 A1 | 5/2004 | |
| WO | WO 2004/041782 A1 | 5/2004 | |
| WO | WO 2004/045518 A2 | 6/2004 | |
| WO | 2004/058682 A1 | 7/2004 | |
| WO | WO 2004/080377 A2 | 9/2004 | |
| WO | WO 2004/110978 A2 | 12/2004 | |
| WO | WO 2005/000309 A2 | 1/2005 | |
| WO | WO 2005/000794 A1 | 1/2005 | |
| WO | WO 2005/000795 A2 | 1/2005 | |
| WO | WO 2005/040136 A1 | 5/2005 | |
| WO | WO 2005/042464 A1 | 5/2005 | |
| WO | WO 2005/049574 A1 | 6/2005 | |
| WO | WO 2005/049580 A1 | 6/2005 | |
| WO | WO 2005/060956 A1 | 7/2005 | |
| WO | 2005/073204 A1 | 8/2005 | |
| WO | WO 2005/073204 A1 | 8/2005 | |
| WO | WO 2005/077925 A1 | 8/2005 | |
| WO | WO 2005/085185 A1 | 9/2005 | |
| WO | WO 2005/086735 A2 | 9/2005 | |
| WO | WO 2005/087232 A1 | 9/2005 | |
| WO | WO 2005/089118 A2 | 9/2005 | |
| WO | WO 2005/090282 A1 | 9/2005 | |
| WO | WO 2005/090328 A1 | 9/2005 | |
| WO | WO 2005/094810 A2 | 10/2005 | |
| WO | WO 2005/099707 A1 | 10/2005 | |
| WO | WO 2005/102998 A1 | 11/2005 | |
| WO | WO 2005/108351 A1 | 11/2005 | |
| WO | WO 2005/111028 A1 | 11/2005 | |
| WO | WO 2005/115361 A2 | 12/2005 | |
| WO | WO 2005/116001 A1 | 12/2005 | |
| WO | WO 2005/120483 A2 | 12/2005 | |
| WO | WO 2006/031715 A1 | 3/2006 | |
| WO | WO 2006/039243 A1 | 4/2006 | |
| WO | WO 2006/044359 A2 | 4/2006 | |
| WO | WO 2006/044707 A1 | 4/2006 | |
| WO | WO 2006/055184 A2 | 5/2006 | |
| WO | WO 2006/060108 A1 | 6/2006 | |
| WO | WO 2006/076317 A2 | 7/2006 | |
| WO | WO 2006/113552 A2 | 10/2006 | |
| WO | WO 2006/124447 A2 | 11/2006 | |
| WO | WO 2006/133216 A2 | 12/2006 | |
| WO | WO 2007/002181 A2 | 1/2007 | |
| WO | WO 2007/005887 A2 | 1/2007 | |
| WO | WO 2007/015567 A1 | 2/2007 | |
| WO | WO 2007/034846 A1 | 3/2007 | |
| WO | WO 2007/061964 A1 | 5/2007 | |
| WO | WO 2007/067490 A1 | 6/2007 | |
| WO | WO 2007/087518 A2 | 8/2007 | |
| WO | WO 2007/099200 A1 | 9/2007 | |
| WO | WO 2007/146914 A1 | 12/2007 | |
| WO | 2008/002490 A2 | 1/2008 | |
| WO | WO 2008/002490 A2 | 1/2008 | |
| WO | WO 2008/008433 A2 | 1/2008 | |
| WO | WO 2008/011072 A2 | 1/2008 | |
| WO | WO 2008/011073 A1 | 1/2008 | |
| WO | WO 2008002490 A2 * | 1/2008 | ........... A61K 31/136 |
| WO | WO 2008/024456 A2 | 2/2008 | |
| WO | WO 2008/042571 A2 | 4/2008 | |
| WO | WO 2008/044033 A1 | 4/2008 | |
| WO | WO 2008/063279 A2 | 5/2008 | |
| WO | WO 2008/063867 A2 | 5/2008 | |
| WO | WO 2008/121602 A1 | 10/2008 | |
| WO | WO 2008/124000 A2 | 10/2008 | |
| WO | WO 2008/124922 A1 | 10/2008 | |
| WO | WO 2008/127717 A1 | 10/2008 | |
| WO | WO 2008/128100 A1 | 10/2008 | |
| WO | WO 2008/130587 A2 | 10/2008 | |
| WO | WO 2009/020234 A2 | 2/2009 | |
| WO | WO 2009/065600 A2 | 5/2009 | |
| WO | WO 2009/081197 A1 | 7/2009 | |
| WO | WO 2009/105214 A2 | 8/2009 | |
| WO | 2009/137104 A1 | 11/2009 | |
| WO | WO 2009/133861 A1 | 11/2009 | |
| WO | WO 2009/137093 A1 | 11/2009 | |
| WO | WO 2009/137104 A1 | 11/2009 | |
| WO | WO 2009/140448 A1 | 11/2009 | |
| WO | WO 2010/022176 A1 | 2/2010 | |
| WO | WO 2010/118287 A1 | 12/2010 | |
| WO | WO 2011/097496 A1 | 8/2011 | |
| WO | 2011/143469 A1 | 11/2011 | |
| WO | WO 2011/140274 A2 | 11/2011 | |
| WO | WO 2011/143469 A1 | 11/2011 | |
| WO | WO 2011/150144 A2 | 12/2011 | |
| WO | WO 2012/047617 A1 | 4/2012 | |
| WO | WO 2012/075375 A1 | 6/2012 | |
| WO | WO 2012/145665 A2 | 10/2012 | |

(56) References Cited

FOREIGN PATENT DOCUMENTS

| WO | WO 2013/082418 A1 | 6/2013 |
|---|---|---|
| WO | WO 2013/082427 A1 | 6/2013 |

OTHER PUBLICATIONS

Loprinzi, C. L., et al., "Management of hot flashes in breast-cancer survivors," Lancet Oncol., 2: 199-204 (2001).
Pandya, K. J., et al., "Pilot study using gabapentin for tamoxifen-induced hot flashes in women with breast cancer," Breast Cancer Research and Treatment, 83: 87-89 (2004).
Stearns, V., et al., "A pilot trial assessing the efficacy of paroxetine hydrochloride (Paxil®) in controlling hot flashes in breast cancer survivors," Annals of Oncology, 11: 17-22 (2000).
"Notification of Transmittal of the International Search Report and the Written Opinion of the International Searching Authority, or the Declaration" from International Application No. PCT/US2007/014598 dated Mar. 28, 2008.
"Notification Concerning Transmittal of Copy of International Preliminary Report on Patentability (Chapter I of the Patent Cooperation Treaty)" from International Application No. PCT/US2007/014598 dated Jan. 15, 2009.
"Notification of Transmittal of the International Search Report and the Written Opinion of the International Searching Authority, or the Declaration" from International Application No. PCT/US2009/002885 dated Sep. 10, 2009.
"Notification Concerning Transmittal of Copy of International Preliminary Report on Patentability Chapter I of the Patent Cooperation Treaty" from International Application No. PCT/US2009/002885 dated Nov. 18, 2010.
"Notification of Transmittal of the International Search Report and the Written Opinion of the International Searching Authority, or the Declaration" from International Application No. PCT/US2011/036311 dated Aug. 12, 2011.
"Notification Concerning Transmittal of Copy of International Preliminary Report on Patentability (Chapter I of the Patent Cooperation Treaty)" from International Application No. PCT/US2011/036311 dated Nov. 22, 2012.
Office Action dated Aug. 15, 2012, from U.S. Appl. No. 12/991,791.
Office Action dated Sep. 10, 2012, from U.S. Appl. No. 12/308,640.
Office Action dated Jul. 16, 2013, from U.S. Appl. No. 12/308,640.
"deuterium." In http://www.britannica.com. Retrieved Feb. 18, 2009 from <http://www.britannica.com/Ebchecked/topic/159684/deuterium>.
Acevedo, S., et al., "Selective Androgen Receptor Modulators Antagonize Apolipoprotein E4-Induced Cognitive Impairments," Letters in Drug Design & Discovery, 5:271-276 (2008).
Allan, G.F., et al., "A Selective Androgen Receptor Modulator that Reduces Prostate Tumor Size and Prevents Orchidectomy-Induced Bone Loss in Rats," J Steroid Biochemistry & Molecular Biology, 103:76-83 (2007).
Allan, G.F., et al., "A Selective Androgen Receptor Modulator with Minimal Prostate Hypertrophic Activity Enhances Lean Body Mass in Male Rats and Stimulates Sexual Behavior in Female Rats," Endocr, 32:41-51 (2007).
Ameri, M., et al., "Demonstrated Solid-State Stability of Parathyroid Hormone PTH(1-34) Coated on a Novel Transdermal Microprojection Delivery System," Pharmaceutical Research, 26(11):2454-2463 (published online Sep. 3, 2009).
Ameri, M., et al., "Parathyroid Hormone PTH(1-34) Formulation that Enables Uniform Coating on a Novel Transdermal Microprojection Delivery System," Pharmaceutical Research, 27(2):303-313 2010 (published online Dec. 15, 2009).
Anderson, A.C., "The Process of Structure-Based Drug Design," Chem and Biol, 10:787-797 (Sep. 2003).
Arun, B., et al., "The Search for the Ideal SERM," Expert Opinion Pharmacotherapy 3(6):681-691 (2002).

Autoimmune disorders: MedlinePlus Medical Encyclopedia [online], [retrieved on Jun. 3, 2011]. Retrieved from the Internet URL:http://www.nlm.nih.gov/medlineplus/ency/article/000816.htm.
Bohl, C.E., "Structural Basis for Antagonism and Resistance of Bicalutamide in Prostate Cancer," PNAS, 102(17):6201-6206 (2005).
Bohl, C.E., et al., "Structural Basis for Accommodation of Nonsteroidal Ligands in the Androgen Receptors," J Biol Chem, 280(45):37747-37754 (Nov. 11, 2005).
Browne, "Stable Isotopes in Pharmaceutical Research," Pharmacochemistry Library, 26:13-18(1997).
Cantin, L., et al., "Structural Characterization of the Human Androgen Receptor Ligand-Binding Domain Complexed with EM5744, a Rationally Designed Steroidal Ligand Bearing a Bulky Chain Directed Toward Helix 12," Journal of Biological Chemistry, 282(42):30910-30919 (Oct. 19, 2007).
Cesnjaj, et al., "In Vivo Models in the Study of Osteopenias," European J Clinical Chemistry and Clinical Biochemistry 29(4):211-219 (1991).
Clinical Trials.gov, "A Study for the Transdermal Application of Teriparatide," Retrieved from: http://www.clinicaltrials.gov/ct2/show/NCT01011556?term=pth+patch&rank=8, Date Retrieved: Sep. 18, 2012, 6 pages.
Clinical Trials.gov, "Dose Ranging Study—Macroflux PTH in Postmenopausal Women With Osteoporosis," Retrieved from: http://www.clinicaltrials.gov/ct2/show/NCT00489918?term=pth+patch&rank=1, Date Retrieved: Sep. 18, 2012, 1 page.
Cosman, F., et al., "Effect of Transdermal Teriparatide Administration on Bone Mineral Density in Postmenopausal Women," J Clin. Endocrinol. Metab., 95(1):151-158 (published online Oct. 26, 2009).
Daddona, Peter E. et al., "Parathyroid Hormone (1-34)-Coated Microneedle Patch System: Clinical Pharmacokinetics and Pharmacodynamics for Treatment of Osteoporosis," Pharm Res, 28:159-165 (2011) (published online Jun. 22, 2010).
Dean, T., "Altered Selectivity of Parathyroid Hormone (PTH) and PTH-Related Protein (PTHrP) for Distinct Conformations of the PTH/PTHrP Receptor", Molecular Endocrinology, 22(1):156-166 (Jan. 2008).
Deschamps, P., et al., "The Saga of Copper(II)-L-histidine," Coordination Chemistry Reviews, 249:295-909 (2005).
Ferrandon, S., et al., "Sustained cyclic AMP production by parathyroid hormone receptor endocytosis", Nature Chemical Biology, 5(10):734-742 (Oct. 2009).
Gao, W., et al., "Comparison of the Pharmacological Effects of a Novel Selective Androgen Receptor Modulator, the 5α-Reductase Inhibitor Finasteride, and the Antiandrogen Hydroxyflutamide in Intact Rats: New Approach for Benign Prostate Hyperplasia," Endocrinology, 145(12):5420-5428 (2004).
Gao, W., et al., "Expanding the Therapeutic use of Androgens via Selective Androgen Receptor Modulators (SARMs)," Drug Discovery Today, 12:241-248 (2007).
Gao, W., et al., "Ockham's Razor and Selective Androgen Receptor Modulators (SARMs): Are we Overlooking the Role of 5α-Reductase?", Molecular Interventions, 7:1013 (2007).
Gao, W., et al., "Selective Androgen Receptor Modulator Treatment Improves Muscle Strength and Body Composition and Prevents Bone Loss in Orchidectomized Rats," Endocrinology, 146(11):4887-4897 (Nov. 2005).
Garland, M.J., et al., "Microneedle arrays as medical devices for enhanced transdermal drug delivery," Expert Rev. Med. Devices 8(4):459-482 (2011).
Gill, H.S. And Prausnitz, M.R., "Coating Formulations for Microneedles," Pharmaceutical Research, 24(7):1369-1380 (2007).
Hamann, L.G., "Discovery and Preclinical Profile of a Highly Potent and Muscle Selective Androgen Receptor Modulator (SARM)," 227th National Meeting of the American Chemical Society Medicinal Chemistry Division, Mar. 28, 2004, Anaheim, CA.

(56) References Cited

OTHER PUBLICATIONS

Hamann, L.G., et al., "Tandem Optimization of Target Activity and Elimination of Mutagenic Potential in a Potent Series of N-aryl Bicyclic Hydantoin-Based Selective Androgen Receptor Modulators," Bioorganic & Medicinal Chemistry Letters, 17:1860-1864 (2007).
Hanada, K., et al., "Bone Anabolic Effects of S-40503, a Novel Nonsteroidal Selective Androgen Receptor Modulator (SARM), in Rat Models of Osteoporosis," Biol. Pharm. Bull., 26(11):1563-1569 (Nov. 2003).
Higuchi, R.I., et al., "Novel Series of Potent, Nonsteroidal, Selective Androgen Receptor Modulators Based on 7H-[1,4]Oxazino[3,2-g]quinolin-7-ones," J Med Chem, 50(10):24862496 (2007).
Hörig, H. And Pullman, W., "From Bench to Clinic and Back: Perspective on the 1st IQPC Translational Research Conference," J Translational Medicine 2(44):1-8 (2004).
Hwang, D.J., et al., "Arylisothiocyanato Selective Androgen Receptor Modulators (SARMs) for Prostate Cancer," Bioorganic & Medicinal Chemistry, 14:6525-6538 (2006).
Kalluri, H. And Banga, A. K., "Transdermal Delivery of Proteins," AAPS PharmSciTech, 12(1) 431-441 (published online Mar. 3, 2011).
Kamberi, M., The effects of sucrose on stability of human brain natriuretic peptide [hBNP(1-32)] and human parathyroid hormone (hPTH(1-34)], J Peptide Res, 66:348-356 (2005).
Katikaneni, S., et al., "Transdermal delivery of ~13 kDa protein-an in vivo comparison of physical enhancement methods", J Drug Targeting, 18(2):141-147 (2010).
Kemppainen, J.A., et al., "Distinguishing Androgen Receptor Agonists and Antagonists: Distinct Mechanisms of Activation by Medroxyprogesterone Acetate and Dihydrotestosterone," Molecular Endocrinology, 13:440-454 (1999).
Kenan, Y., et al., "Comparison of Transdermal and Subcutaneous Teriparatide Pharmacokinetics and Pharmacodynamics of Bone Markers in Postmenopausal Women," Poster Session, Presentation No. FR0376 of the ASBMR 2010 Annual Meeting, (Oct. 15th-16th 2010).
Kilbourne, E.J., et al., "Selective Androgen Receptor Modulators for Frailty and Osteoporosis," Current Opinion in Investigational Drugs, 8(10):821-829 (2007).
Kim, J., et al., "The 4-Para Substituent of S-3-(phenoxy)-2-hydroxy-2-methyl-N-(4-nitro-3-trifluoromethyl-phenyl)-propionamides is a Major Structural Determinant of in Vivo Disposition and Activity of Selective Androgen Receptor Modulators," Jpet #88344, DOI:10.1124/jpet.105.088344, 42 pages (Jun. 29, 2005).
Kinoyama, I., et al., "(+)-(2R,55)-444-Cyano-3-(trifluoromethyl)phenyl]-2,5-dimethyl-N[6-(trifluoromethyl)pyridin-3-yl]piperazine-1-carboxamide (YM580) as an Orally Potent and Peripherally Selective Nonsteroidal Androgen Receptor Antagonist," J Med Chem 49(2): 716-726 (2006).
Lanter, J.C., et al., "The Discovery of a Potent Orally Efficacious Indole Androgen Receptor Antagonist Through in vivo Screening," Bioorganic & Medicinal Chemistry Letters, 17:123-126 (2007).
Lloyd, M.E., et al., "Relation Between Insulin-Like Growth Factor-1 Concentrations, Osteoarthritis, Bone Density, and Fractures in the General Population: the Chingford Study," Ann Rheum Dis, 55:870-874 (1996).
Loprinzi, C.L., et al., "Management of Hot Flashes in Breast-Cancer Survivors," The Lancet Oncology, 2(4):199-204 (Apr. 2001).
Ma, Y.L., et al., "Raloxifene and Teriparatide (hPTH 1-34) Have Complementary Effects on the Osteopenic Skeleton of Ovariectomized Rats," J Bone Mineral Metab, 23 (Supp.) 62-68 (2005).
Martinborough, E., et al., "Substituted 6-(1-pyrrolidine)-quinolin-2(1H)-ones as Novel Selective Androgen Receptor Modulators." J Med Chem 50:5049-52 (2007).
McGinley, P.L., et al., "Circumventing Anti-Androgen Resistance by Molecular Design," J Am Chem Soc, 129:3822-3823 (2007).

Medi, B.M. and Singh, J., "Electronically Facilitated Transdermal Delivery of Human Parathyroid Hormone (1-34)," International J Pharmaceutics, 263:25-33 (2003).
Mesu, J. G., et al., "Infrared and Raman Spectroscopic Study of pH-induced Structural Changes of L-histidine in Aqueous Environment," Vibrational Spectroscopy, 39:114-125 (2005).
Miao, D., et al., "Osteoblast-derived PTHrP is a potent endogenous bone anabolic agent that modifies the therapeutic efficacy of administered PTH 1-34," J Clinical Investigation, 115(9):2402-2411 (Sep. 2005).
Miller, C.P., et al., "Design, Synthesis, and Preclinical Characterization of the Selective Androgen Receptor Modulator (Sarm) RAD140," ACS Med Chem Lett, 2(2):124-129, DOI: 10.1021/ml11002508 (Dec. 2, 2010).
Miller, C.P., et al., "Synthesis of Potent, Substituted Carbazoles as Selective Androgen Receptor Modulators (SARMs)," Bioorg Med Chem Lett, 20:7516-7520 (2010).
Mitchell, H.J., et al., Design, Synthesis, and Biological Evaluation of 16-Substituted 4-Azasteroids as Tissue-Selective Androgen Receptor Modulators (SARMs), J Med Chem, 52(15):4578-81 (2009).
Mohler, M.L., et al., "Nonsteroidal Selective Androgen Receptor Modulators (SARMs): Dissociating the Anabolic and Androgenic Activities of the Androgen Receptor for Therapeutic Benefit," J Med Chem, 52(12):3597-617 (Jun. 25, 2009).
Morris, J.J., et al., "Non-steroidal Antiandrogens. Design of Novel Compounds Based on an Infrared Study of the Dominant Conformation and Hydrogen-Bonding Properties of a Series of Anilide Antiandrogens," J Med Chem, 34:447-455 (1991).
Ng, R.A., "Synthesis and Sar of Potent and Selective Androgen Receptor Antagonists: 5,6-Dicholoro-benzimidazole Derivatives," Bioorganic & Medicinal Chemistry Letters, 17:784-788 (2007).
Ng, R.A., "Synthesis of Potent and Tissue-Selective Androgen Receptor Modulators (SARMs): 2-(2,2,2)-Trifluoroethyl-benzimidazole Scaffold," Bioorganic & Medicinal Chemistry Letters, 17:1784-1787 (2007).
Obinata, R., et al., "Stereodivergent Construction of Aminidiols with a CF3 Group," Organic Letters 12(19):4316-9 (2010).
Okazaki, M., et al., "Prolonged signaling at the parathyroid hormone receptor by peptide ligands targeted to a specific receptor conformation," PNAS, 105(43):16525-16530 (Oct. 28, 2008).
Ornoy, et al., "Osteoporosis: Animal Models for the Human Disease," Animal Models of Human Related calcium Metabolic Disorders, 105-126 (1995).
Ostrowski, J., et al., "Pharmacological and X-Ray Structural Characterization of a Novel Selective Androgen Receptor Modulator: Potent Hyperanabolic Stimulation of Skeletal Muscle with Hypostimulation of Prostate in Rats," Endocrinology, 148(1):4-12 (Jan. 2007).
Pandya, K.J., et al., "Pilot Study Using Gabapentin for Tamoxifen-Induced Hot Flashes in Woment with Breast Cancer," Breast Cancer Research and Treatment, 83:87-89 (2004).
Paudel, K.S., et al., "Challenges and opportunities in dermal/transdermal delivery," Ther Deliv, 1(1):109-131 (Jul. 2010).
Perumal, O., et al., "Turning Theory into Practice: The Development of Modern Transdermal Drug Delivery systems and Future Trends," Skin Pharmacol Physiol, 26:331342 (Jul. 2013).
Piu, F., et al., "Pharmacological Characterization of AC-262536, A Novel Selective Androgen Receptor Modulator," J Steroid Biochemistry & Molecular Biology, 109:129-137 (2008).
Riedmaier, I., et al., "Influence of testosterone and a Novel SARM on Gene Expression in Whole Blood of Macaca fascicularis," J Steroid Biochemistry and Molecular Biology, 114:167-173 (2009).
Rochira, V., et al., "Osteoporosis and Male Age-Related Hypogonadism: Role of Sex Steroids on Bone (patho)Physiology," Eur J Endocrinol, 154:175-185 (2006).
Rosenblatt, M., "When two keys fit one lock, surprises follow", Nature Chemical Biology, 5(10):707-708 (Oct. 2009).
Salvati, M.E., et al., "Identification and Optimization of a Novel Series of [2.2.1]-oxabicyclo imide-based Androgen Receptor Antagonists," Bioorganic & Medicinal Chemistry Letters, 18:1910-1915 (2008).

(56) References Cited

OTHER PUBLICATIONS

Schafer, S. and Kokhof, P., "Failure is an Option: Learning From Unsuccessful Proofof-Concept Trials," Drug Discovery Today, 13(21/22):913-916 (2008).
Stellman, J.T., "Development, Production and Characterization of Plastic Hypodermic Needles," MS Thesis, Georgia Institute of Technology, pp. 1-150 (2009).
Sterns, V., et al., "A Polot Trial Assessing the Efficicy of Paroxetine Hydrochloride (Paxil©) in Controlling Hot Flashes in Breast Cancer Survivors," Annals of Oncoogy, 11:17-22 (2000).
Sun, C., et al. "Discovery of Potent, Orally-Active, and Muscle-Selective Androgen Receptor Modulators Based on an N-Aryl-hydroxybicyclohydantoin Scaffold," J Med Chem, 49(26):7596-7599 (2006).
Sundar, et al., "Spironolactone, a possible selective androgen receptor modulator, should be used with caution in patients with metastatic carcinoma of the prostate," Bmj Case Rep. (Feb. 25, 2012), Abstract.
Suzuki, Y., et al., "Iontophoretic Pulsatile Transdermal Delivery of Human Parathyroid Hormone (1-34)," J Pharmacy and Pharmacology, 53(9):1227-1234 (2001).
Thiel, K.A., "Structure-aided drug design's next generation," Nature Biotechnol, 22(5):513-519 (May 2004).
Tucker, H., et al., "Nonsterodial Antiandrogens, Synthesis and Structure-Activity Relationships of 3-Substituted Derivatives of 2-Hydroxypropionanilides," J Med Chem, 31:954-959 (1988).
Vajda, E.G., et al., Pharmacokinetics and Pharmacodynamics of LGD-3303 [9-Cholor-2- ethyl-1-methyl-3-(2,2,2-trifluoroethyl)-3H-pyrrolo-[3,24]quinolin-7(6H)-one], an Orally Available Nonsteroidal-Selective Androgen Receptor Modulator, The Journal of Pharmacology and Experimental Therapeutics, 328(2):663-670 (2009).
Van der Maaden, K., et al., "Microneedle technologies for (trans) dermal drug and vaccine delivery", J Controlled Release, 161:645-655 (2012).
Van Oeveren, A., et al., "Novel Selective Androgen Receptor Modulators: SAR Studies on 6-bisalkylamino-2-quinolinones," Bioorganic & Medicinal Chemistry Letters, 17:15271531 (2007).
Wang, Z. et al., "Anti-Inflammatory Properties and Regulatory Mechanism of a Novel Derivative of Artemisinin in Experimental Autoimmune Encephalomyelitis," J Immunol 179:5958-5965 (2007).
Wright, P., "Transdermal Drug Delivery Looks for New Frontiers," Pharmaceutical Commerce, Feb. 26, 2013.
Zeng, C., et al., "Efficient Synthesis of (2R,3S)-2-amino-3-(benzyloxy)-4,4,4- trifluorobutanoic acid (4,4,4-trifluoro-OBn-D-allothreonine)," Tetrahedron Letters, 51:53615363 (2010).
Zhang, X., et al., "Design, Synthesis, and in Vivo SAR of a Novel Series of Pyrazolines as Potent Selective Androgen Receptor Modulators," J Med Chem, 50(16):3857-3869 (2007).
Zhang, X., et al., "Synthesis and SAR of Novel Hydantoin Derivatives as Selective Androgen Receptor Modulators," Bioorganic & Medicinal Chemistry Letters, 16:5763-5766 (2006).
Zizic, T.M., et al., "Pharmacologic Prevention of Osteoporotic Fractures," Am Fam Physician, 70:1293-1300 (2004).
Australian Patent Office, International Search Report for PCT/US2011/063034 completed Mar. 15, 2012 and mailed Mar. 19, 2012.
Chinese Patent Office, Chinese Patent Search Report for 201280030749X dated Feb. 16, 2015.
European Patent Office, International Search Report for PCT/EP1996/01962 mailed Sep. 16, 1996.
European Patent Office, International Search Report for PCT/US1997/22498 mailed Dec. 23, 1998.
European Patent Office, International Preliminary Report on Patentability (Ch I) for PCT/US2007/014598 issued Jan. 6, 2009.
European Patent Office, International Search Report and Written Opinion for PCT/US2007/014598 mailed Mar. 28, 2008.
European Patent Office, International Preliminary Report on Patentability (Ch I) for PCT/US2007/021216 issued May 26, 2009.
European Patent Office, International Search Report and Written Opinion for PCT/US2007/021216 mailed Sep. 25, 2008.
European Patent Office, International Preliminary Report on Patentability (Ch I) for PCT/US2009/001035 issued Aug. 24, 2010.
European Patent Office, International Search Report and Written Opinion for PCT/US2009/001035 mailed Aug. 7, 2009.
European Patent Office, International Preliminary Report on Patentability (Ch I) for PCT/US2009/002868 issued Nov. 9, 2010.
European Patent Office, International Search Report and Written Opinion for PCT/US2009/002868 mailed Aug. 3, 2009.
Cl 00 European Patent Office, International Preliminary Report on Patentability (Ch I) for PCT/US2009/002885 issued Nov. 9, 2010.
European Patent Office, International Search Report and Written Opinion for PCT/US2009/002885 mailed Sep. 10, 2010.
C102 European Patent Office, International Preliminary Report on Patentability (Ch I) for PCT/US2011/053375 issued Apr. 2, 2013.
C103 European Patent Office, International Search Report and Written Opinion for PCT/US2011/053375 mailed Jan. 16, 2012.
European Patent Office, Extended Search Report for PCT/US2011/023768 (EP11740437, W02011097496) mailed Apr. 26, 2013.
Korean Intellectual Property Office, International Search Report for PCT/US2006/044921 mailed Mar. 15, 2007.
C106 United States Patent and Trademark Office, International Search Report for PCT/US1996/011292 mailed Oct. 16, 1996.
C107 United States Patent and Trademark Office, International Search Report and Written Opinion for PCT/US2009/054348 mailed Dec. 9, 2009.
United States Patent and Trademark Office, International Preliminary Report on Patentability (Ch I) for PCT/US2010/030480 issued Oct. 11, 2011.
United States Patent and Trademark Office, International Search Report and Written Opinion for PCT/US2010/030480 mailed Jun. 9, 2010.
United States Patent and Trademark Office, International Preliminary Report on Patentability (Ch I) for PCT/US2011/023768 issued Aug. 7, 2012.
United States Patent and Trademark Office, International Search Report and Written Opinion for PCT/US2011/023768 mailed Mar. 25, 2011.
United States Patent and Trademark Office, International Preliminary Report on Patentability (Ch I) for PCT/US2011/036311 issued Nov. 13, 2012.
United States Patent and Trademark Office, International Search Report and Written Opinion for PCT/US2011/036311 mailed Aug. 12, 2011.
United States Patent and Trademark Office, International Preliminary Report on Patentability (Ch I) for PCT/US2012/034510 issued Mar. 18, 2014.
United States Patent and Trademark Office, International Search Report and Written Opinion for PCT/US2012/034510 mailed Aug. 31, 2012.

* cited by examiner

THERAPEUTIC REGIMENS

RELATED APPLICATION

This application is a continuation of U.S. application Ser. No. 13/697,230, filed Nov. 9, 2012, which is the U.S. National Stage of International Application No. PCT/US2011/036311, filed May 12, 2011, which designates the U.S., published in English, and claims the benefit of U.S. Provisional Application No. 61/334,095, filed May 12, 2010. The entire teachings of the above application are incorporated herein by reference.

BACKGROUND OF THE INVENTION

The compound of formula I ((R)-6-(2-(ethyl(4-(2-(ethylamino)ethyl)-benzyl)amino)-4-methoxyphenyl)-5,6,7,8-tetrahydronaphthalen-2-ol) and it salts are described and claimed in U.S. Pat. No. 7,612,114 B2, the entire content of which is hereby incorporated by reference.

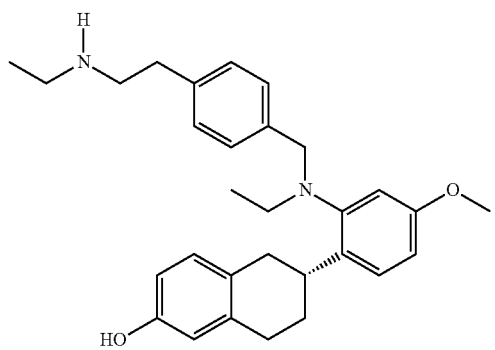

Use of the compound formula I for the treatment of vasomotor symptoms is described in WO2008/002490 also incorporated herein by reference in its entirety. While the effectiveness of compound 1 and its salts in the treatment of vasomotor symptoms has been described, improved dosing regimens would benefit those suffering from vasomotor symptoms.

SUMMARY OF THE INVENTION

This invention relates to clinically useful therapeutic dosing regimens for the compound of formula I ((R)-6-(2-(ethyl(4-(2-(ethylamino)ethyl)benzyl)amino)-4-methoxyphenyl)-5,6,7,8-tetrahydronaphthalen-2-ol) or its salts.

This invention also includes unit dosage forms containing the compound of formula I ((R)-6-(2-(ethyl(4-(2-(ethylamino)ethyl)benzyl)amino)-4-methoxyphenyl)-5,6,7,8-tetrahydronaphthalen-2-ol) or its salts.

In certain embodiments, this invention includes a unit dosage form suitable for administration to a human comprising 10 mg of the compound of formula I as a salt

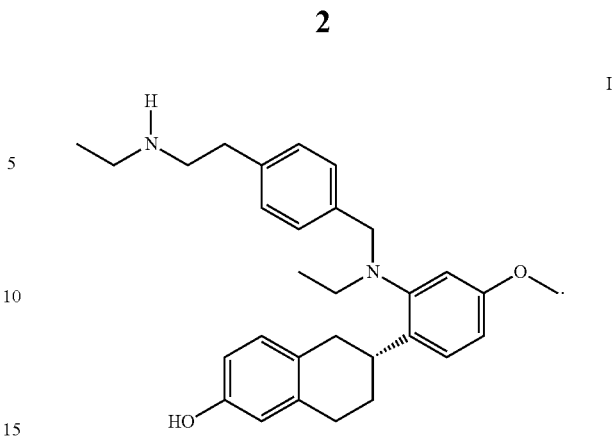

In a particular embodiment, the 10 mg of the compound of Formula 1 is present as its dihydrochloride salt.

In another particular embodiment, the 10 mg of the compound of Formula 1 is present as an acid addition salt.

In yet another particular embodiment, the 10 mg of the compound of Formula 1 is present as its hydrogen chloride salt.

In certain embodiments, this invention includes a unit dosage form suitable for administration to a human comprising 5 mg of the compound of formula I as a salt (e.g., an acid addition salt, dihydrochloride salt or hydrogen chloride salt).

In certain embodiments, this invention includes a unit dosage form suitable for administration to a human comprising 2.5 mg of the compound of formula I as a salt (e.g., an acid addition salt, dihydrochloride salt or hydrogen chloride salt).

In certain embodiments, this invention includes a unit dosage form suitable for administration to a human comprising 1 mg of the compound of formula I as a salt (e.g., an acid addition salt, dihydrochloride salt or hydrogen chloride salt).

In some embodiments, the unit dosage form comprising the compound of formula I contains 1 mg, 2.5 mg, 5 mg or 10 mg as a salt (e.g., an acid addition salt, dihydrochloride salt or hydrogen chloride salt).

In some embodiments, the unit dosage form comprising the compound of formula I contains 1 mg, 2.5 mg, 5 mg or 10 mg as a hydrochloride salt.

In some embodiments, the unit dosage form comprising the compound of formula I contains 1 mg, 2.5 mg, 5 mg or 10 mg as a dihydrochloride salt.

In some embodiments, the unit dosage form comprising the compound of formula I contains 1 mg, 2.5 mg, 5 mg or 10 mg as a salt, wherein said salt is a hydrogen chloride salt wherein said hydrogen chloride is present in a stoichiometry of at least one hydrogen chloride molecule but no more than 2.1 hydrogen chloride molecules for each molecule of formula I.

In one aspect, the unit dosage form is for once daily administration. In another aspect, the unit dosage form is for oral administration. In yet another aspect the unit dosage form is suitable for once daily, oral administration.

In some instances, the unit dosage form further comprises one or more pharmaceutically acceptable excipients.

In certain embodiments, the dosage form unit is a tablet or capsule suitable for oral administration.

In certain embodiments, the dosage unit form, after administration, is essentially dissolved in the stomach prior to being released into the small intestines.

In some instances, the dosage form unit is not coated with an acid resistant coating.

In certain embodiments, the intended human is a woman.

This invention also includes methods of treating vasomotor disturbances in a peri- or post-menopausal woman in need thereof comprising administering to the woman a unit dosage form comprising 10 mg of the compound of formula I ((R)-6-(2-(ethyl(4-(2-(ethylamino)ethyl)benzyl)amino)-4-methoxyphenyl)-5,6,7,8-tetrahydronaphthalen-2-ol) as a salt (e.g., an acid addition salt, dihydrochloride salt or hydrogen chloride salt).

This invention also includes methods of treating vasomotor disturbances in a peri- or post-menopausal woman in need thereof comprising administering to the woman a unit dosage form comprising 10 mg of the compound of formula I ((R)-6-(2-(ethyl(4-(2-(ethylamino)ethyl)benzyl)amino)-4-methoxyphenyl)-5,6,7,8-tetrahydronaphthalen-2-ol) as its dihydrochloride salt.

This invention also includes methods of treating vasomotor disturbances in a post-menopausal woman in need thereof comprising administering to the woman a unit dosage form containing 10 mg of (R)-6-(2-(ethyl(4-(2-(ethylamino)ethyl)benzyl)amino)-4-methoxyphenyl)-5,6,7,8-tetrahydronaphthalen-2-ol as a salt (e.g., an acid addition salt, dihydrochloride salt or hydrogen chloride salt).

This invention also includes methods of treating vasomotor disturbances in a post-menopausal woman in need thereof comprising administering to the woman a unit dosage form containing 10 mg of (R)-6-(2-(ethyl(4-(2-(ethylamino)ethyl)benzyl)amino)-4-methoxyphenyl)-5,6,7,8-tetrahydronaphthalen-2-ol as its dihydrochloride salt.

In some instances, the methods of this invention comprise the once-daily, oral administration of 10 mg of (R)-6-(2-(ethyl(4-(2-(ethylamino)ethyl)benzyl)amino)-4-methoxyphenyl)-5,6,7,8-tetrahydronaphthalen-2-ol as its salt (e.g., an acid addition salt, dihydrochloride salt or hydrogen chloride salt).

In some instances, the methods of this invention comprise the once-daily, oral administration of 10 mg of (R)-6-(2-(ethyl(4-(2-(ethylamino)ethyl)benzyl)amino)-4-methoxyphenyl)-5,6,7,8-tetrahydronaphthalen-2-ol as its dihydrochloride salt.

This invention also includes methods of treating vasomotor disturbances in a peri- or post-menopausal woman in need thereof comprising administering to the woman a unit dosage form comprising 1 mg, 2.5 mg or 5 mg of the compound of formula I ((R)-6-(2-(ethyl(4-(2-(ethylamino)ethyl)benzyl)amino)-4-methoxyphenyl)-5,6,7,8-tetrahydronaphthalen-2-ol) as a salt (e.g., an acid addition salt, dihydrochloride salt or hydrogen chloride salt).

This invention also includes methods of treating vasomotor disturbances in a peri- or post-menopausal woman in need thereof comprising administering to the woman a unit dosage form comprising 1 mg, 2.5 mg or 5 mg of the compound of formula I ((R)-6-(2-(ethyl(4-(2-(ethylamino)ethyl)benzyl)amino)-4-methoxyphenyl)-5,6,7,8-tetrahydronaphthalen-2-ol) as its dihydrochloride salt.

This invention also includes methods of treating vasomotor disturbances in a post-menopausal woman in need thereof comprising administering to the woman a unit dosage form containing 1 mg, 2.5 mg or 5 mg of (R)-6-(2-(ethyl(4-(2-(ethylamino)ethyl)benzyl)amino)-4-methoxyphenyl)-5,6,7,8-tetrahydronaphthalen-2-ol as its salt (e.g., an acid addition salt, dihydrochloride salt or hydrogen chloride salt).

This invention also includes methods of treating vasomotor disturbances in a post-menopausal woman in need thereof comprising administering to the woman a unit dosage form containing 1 mg, 2.5 mg or 5 mg of (R)-6-(2-(ethyl(4-(2-(ethylamino)ethyl)benzyl)amino)-4-methoxyphenyl)-5,6,7,8-tetrahydronaphthalen-2-ol as its dihydrochloride salt.

In some instances, the methods of this invention comprise the once-daily, oral administration of 1 mg, 2.5 mg or 5 mg of (R)-6-(2-(ethyl(4-(2-(ethylamino)ethyl)benzyl)amino)-4-methoxyphenyl)-5,6,7,8-tetrahydronaphthalen-2-ol as its salt (e.g., an acid addition salt, dihydrochloride salt or hydrogen chloride salt).

In some instances, the methods of this invention comprise the once-daily, oral administration of 1 mg, 2.5 mg or 5 mg of (R)-6-(2-(ethyl(4-(2-(ethylamino)ethyl)benzyl)amino)-4-methoxyphenyl)-5,6,7,8-tetrahydronaphthalen-2-ol as its dihydrochloride salt.

In some embodiments, the dosage form unit is a tablet or capsule suitable for oral administration.

In some embodiments, the methods of this invention administer a unit dosage form that, after administration, is essentially dissolved in the stomach prior to being released into the small intestines.

In some instances, the methods of this invention administer a unit dosage form that is not coated with an acid resistant coating.

This invention also includes methods of treating vasomotor disturbances in a peri- or post-menopausal woman comprising administering to the woman a compound of formula I ((R)-6-(2-(ethyl(4-(2-(ethylamino)ethyl)benzyl)amino)-4-methoxyphenyl)-5,6,7,8-tetrahydronaphthalen-2-ol) or a salt thereof wherein said administration results in a steady state plasma $C_{max}$ of from 0.40 ng/mL to 1.44, such as from 0.40 ng/mL to 1.43 ng/mL. In certain related embodiments, said administration results in a steady state $C_{max}$ of from 0.22 ng/mL to 1.61 ng/mL. In one aspect, the compound of formula I is in the form of a salt (e.g., an acid addition salt, dihydrochloride salt or hydrogen chloride salt).

In another aspect, the compound of formula is orally administered, once-daily. In yet another aspect, the compound that is administered orally, once-daily is in a unit dosage form. In a further aspect, the unit dosage form is a tablet or a capsule.

This invention also includes methods of treating vasomotor disturbances in a post-menopausal woman comprising administering to the woman a compound of formula I ((R)-6-(2-(ethyl(4-(2-(ethylamino)ethyl)benzyl)amino)-4-methoxyphenyl)-5,6,7,8-tetrahydronaphthalen-2-ol) wherein said administration results in a steady state plasma $C_{max}$ of from 0.40 ng/mL to 1.44 ng/mL, such as from 0.40 ng/mL to 1.43 ng/mL. In certain related embodiments, said administration results in a steady state $C_{max}$ of from 0.22 ng/mL to 1.61 ng/mL. In one aspect, the compound is administered once-daily. In another aspect, the compound is administered orally, once-daily.

In some embodiments, (R)-6-(2-(ethyl(4-(2-(ethylamino)ethyl)benzyl)amino)-4-methoxyphenyl)-5,6,7,8-tetrahydronaphthalen-2-ol is administered as its dihydrochloride salt.

This invention also includes methods of treating vasomotor disturbances in a peri- or post-menopausal woman comprising the administering of (R)-6-(2-(ethyl(4-(2-(ethylamino)ethyl)benzyl)amino)-4-methoxyphenyl)-5,6,7,8-tetrahydronaphthalen-2-ol wherein said daily administration results in a steady state trough level of from 0.11 ng/mL to 0.79 ng/mL or from 0.12 ng/mL to 0.86 ng/mL. In some embodiments, (R)-6-(2-(ethyl(4-(2-(ethylamino)ethyl)benzyl)amino)-4-methoxyphenyl)-5,6,7,8-tetrahydronaphthalen-2-ol is administered as its salt (e.g., an acid addition salt, dihydrochloride salt or hydrogen chloride salt).

In some aspects, this invention also includes methods of treating vasomotor disturbances in post-menopausal women comprising the daily administration of (R)-6-(2-(ethyl(4-(2-(ethylamino)ethyl)benzyl)amino)-4-methoxyphenyl)-5,6,7,8-tetrahydronaphthalen-2-ol wherein said administration results in a steady state plasma $C_{max}$ of from 0.40 ng/mL to 1.43 ng/mL or a steady state plasma $C_{max}$ of from 0.22 ng/mL to 1.61 ng/mL and a steady state trough plasma level of from 0.11 ng/mL to 0.79 ng/mL or from 0.12 ng/mL to 0.86 ng/mL. In some embodiments, (R)-6-(2-(ethyl(4-(2-(ethylamino)ethyl)benzyl)amino)-4-methoxyphenyl)-5,6,7,8-tetrahydronaphthalen-2-ol is administered as its salt (e.g., an acid addition salt, dihydrochloride salt or hydrogen chloride salt).

In certain embodiments of this invention, the one or more delineated pharmacokinetic parameters are achieved by the administration of (R)-6-(2-(ethyl(4-(2-(ethylamino)ethyl)benzyl)amino)-4-methoxyphenyl)-5,6,7,8-tetrahydronaphthalen-2-ol as a once-daily, oral administration of a unit dosage form. In some instances, the unit dosage form is a capsule or tablet. In certain embodiments, the capsule or tablet is essentially dissolved in the stomach prior to being released into the small intestines. In some embodiments, the dosage form unit is not coated with an acid resistant coating.

In some embodiments of this invention, the one or more delineated pharmacokinetic parameters are achieved by the administration of (R)-6-(2-(ethyl(4-(2-(ethylamino)ethyl)benzyl)amino)-4-methoxyphenyl)-5,6,7,8-tetrahydronaphthalen-2-ol as a once-daily, oral administration of a dosage form unit comprising 10 mg of the compound as its salt (e.g., an acid addition salt, dihydrochloride salt or hydrogen chloride salt).

In some instances, the dosage form unit is a capsule or tablet. In certain embodiments, the capsule or tablet is essentially dissolved in the stomach prior to being released into the small intestines. In some embodiments, the dosage form unit is not coated with an acid resistant coating.

In some embodiments of this invention, the one or more delineated pharmacokinetic parameters are achieved by the administration of (R)-6-(2-(ethyl(4-(2-(ethylamino)ethyl)benzyl)amino)-4-methoxyphenyl)-5,6,7,8-tetrahydronaphthalen-2-ol as a once-daily, oral administration of a dosage form unit comprising 1 mg, 2.5 mg or 5 mg of the compound as its salt (e.g., an acid addition salt, dihydrochloride salt or hydrogen chloride salt).

In some instances, the dosage form unit is a capsule or tablet. In certain embodiments, the capsule or tablet is essentially dissolved in the stomach prior to being released into the small intestines. In some embodiments, the dosage form unit is not coated with an acid resistant coating.

DETAILED DESCRIPTION OF THE INVENTION

Figure 1:
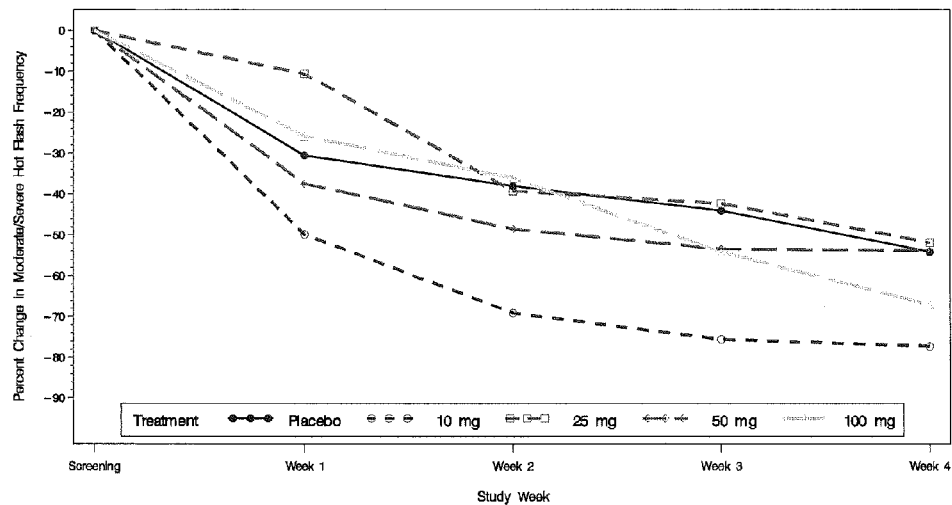
FIG. 1 is a graph showing the reduction in mean weekly frequency of moderate and severe hot flashes (Safety/Intent-to-treat population (ITT)).

During the period immediately leading up to the menopausal period and usually for 1 or even many more years after, many women experience various central nervous system (CNS) disturbances associated with decreasing and/or fluctuating hormone levels (ie estrogens and progestins) brought on by the shutdown of ovarian function. The side effects are variously described but most prominently include an uncomfortable heating of the skin, usually on the upper body and most often in the face and neck. The sensations are transitory in nature, typically less than 30 minutes in duration. The sensation of heat can be accompanied by sweating, accelerated heart rate and a significant amount of physical discomfort. These sensations are typically referred to as hot flashes or hot flushes and may occur not only in the day but at night as well. Beyond the hot flashes or hot flushes associated with menopause, women might experience additional CNS disturbances. For example, some women experience depression, irritability, mood swings and other emotional or mood disorders as a consequence of the declining and/or fluctuating hormone levels associated with the menopause period. It has been known for some time that if women supplement their declining and/or fluctuating hormone levels with estrogens and/or progestins, these side effects can be largely, if not completely, eliminated. However, depending on the particular treatment modality being employed, the use of these hormones in postmenopausal women can be associated with certain side effects including the possibility of increased risk for breast cancer, uterine bleeding, uterine cancer, stroke, blood clots and even heart disease. Not surprisingly, researchers have for some time been trying to find therapies that will treat the hormone-associated CNS effects of the menopausal period while avoiding some, and preferably all of the side effects.

The results of a phase 2a clinical study assessing the effects of the selective estrogen receptor modulator (SERM) (R)-6-(2-(ethyl(4-(2-(ethylamino)ethyl)benzyl)amino)-4-methoxyphenyl)-5,6,7,8-tetrahydronaphthalen-2-ol on women suffering from hot flushes are reported herein. The preclinical data for (R)-6-(2-(ethyl(4-(2-(ethylamino)ethyl)benzyl)amino)-4-methoxyphenyl)-5,6,7,8-tetrahydronaphthalen-2-ol indicate that it does not stimulate estrogen-dependent proliferation of mammary carcinoma cells (MCF-7) cells in the same way as protypical estrogen agonists (e.g. estradiol) and in fact, is a potent antagonist of estradiol stimulation on these cells, suggesting that this compound will not increase the risk of breast cancer in women taking the drug and possibly could even decrease that risk. Moreover, in preclinical rat models measuring estrogenic agonist effects on the endometrium, (R)-6-(2-(ethyl(4-(2-(ethylamino)ethyl)benzyl)amino)-4-methoxyphenyl)-5,6,7,8-tetrahydronaphthalen-2-ol dihydrochloride demonstrates negligible estrogen agonist stimulation effects. This indicates that (R)-6-(2-(ethyl(4-(2-(ethylamino)ethyl)benzyl)amino)-4-methoxyphenyl)-5,6,7,8-tetrahydronaphthalen-2-ol dihydrochloride is unlikely to cause unacceptable uterine stimulation in postmenopausal women.

For purposes of this invention, a dihydrochloride salt means that the base compound (R)-6-(2-(ethyl(4-(2-(ethylamino)ethyl)benzyl)amino)-4-methoxyphenyl)-5,6,7,8-tetrahydronaphthalen-2-ol has from 1.6 to 2 HCl's associated with the molecule. In some embodiments, a dihydrochloride salt refers to the base compound (R)-6-(2-(ethyl(4-(2-(ethylamino)ethyl)benzyl)amino)-4-methoxyphenyl)-5,6,7,8-tetrahydronaphthalen-2-ol wherein that base compound has from 1.8 to 2 HCl's associated with it. In certain embodiments, the term dihydrochloride refers to the base compound with approximately 2HCl's associated with it.

For purposes of this invention, a "unit dosage form" is a dosage form that is a discrete dosage formulation meaning that the entire drug content to be administered at a single time is contained in a single dosage form unit. For example, pills, tablets, lozenges, capsules are all dosage form units for purposes of this invention. Also contemplated in the scope of this definition is the possibility that the drug or some component of the drug formulation is not a single dosage form but only that the dose to be administered as a whole is a discrete unit. This means that a capsule may contain granules of the drug within the capsule but it is a single capsule that is to be administered. Likewise, a lozenge may contain the drug substance dissolved in a matrix but the drug form is the lozenge itself and thus is a unit dosage formulation.

The "unit dosage form" can be administered to a patient or preferably self-administered by a patient in a form that is generally acceptable in the pharmaceutical venue. In other word, the unit dosage form is pharmaceutically useful. By way of non-limiting example, pharmaceutically useful dosage forms are suitable for oral delivery and include pills, tablets, buccal tablets, orally-disintegrating tablets, thin films, chewable tablets, lozenges, sublingual tablets or pills, liquid solutions, suspensions, syrups, powder or granules suitable for sprinkling in food or beverages capsules, food or candy with the drug contained within.

Pharmaceutically acceptable excipients include those excipients that are generally regarded as safe for administration to humans. Excipients especially suitable for formulations suitable for oral delivery include diluents (monosaccharides, disaccharides and polyhydric alcohols including starch, mannitol, dextrose, sucrose, microcrystalline cellulose, maltodextrin, sorbitol, xylitol, fructose and the like), binders (starch, gelatin, natural sugars, gums, waxes and the like), disintegrants (alginic acid, carboxymethylcellulose (calcium or sodium), cellulose, crocarmellose, crospovidone, microcrystalline cellulose, sodium starch glycolate, agar and the like), acidic or basic buffering agents (citrates, phosphates, gluconates, acetates, carbonates, bicarbonates and the like), chelating agents (edetic acid, edetate calcium, edetate disodium and the like), preservatives (benzoic acid, chlorhexidine gluconate, potassium benzoate, potassium sorbate, sorbic acid, sodium benzoate and the like), glidants and lubricants (calcium stearate, oils, magnesium stearate, magnesium trisilicate, sodium fumarate, colloidal silica, zinc stearate, sodium oleate, stearic acid, and the like), antioxidants and/or preservatives (tocopherols, ascorbates, phenols, and the like) and acidifying agents (citric acid, fumaric acid, malic acid, tartaric acid and the like) as well as coloring agents, coating agents, flavoring agents, suspending agents, dessicants, humectants and other excipients known to those of skill in the art.

The unit dosage formulations or unit dosage forms of this invention can be prepared in different forms including most commonly, tablets and capsules. The tablets can be formulated by a wide variety of methods known to one of skill in the art including, for example, preparing a dry powder mixture of the drug substance in combination with one or more of the excipients granulating the mixture and pressing to together into a tablet and optionally coating the tablet with an enteric or non-enteric coating. The final coat typically includes a light protective pigment such as titanium oxide and a shellac or wax to keep the tablet dry and stable. While not intending to be limited by theory or example, in some instances it might be preferred to prepare the tablets by wet granulating the drug with one or more of the excipients and then extruding the granulated material.

The unit dosage formulations or unit dosage forms of this invention also include capsules wherein the drug is enclosed inside the capsule either as a powder together with optional excipients or as granules containing usually including one or more excipients together with the drug and wherein the granule in turn can be optionally coated, for example, enterically or non-enterically.

The formulations of this invention may be solids and when present as solids, they maybe of defined particle size. It maybe sometimes preferable to administer the compound with a certain particle size—a particle size with a preferred range where the average mean particle size diameter is under 100 microns, or 75 microns, or 50 microns, or 35 microns, or 10 microns or 5 microns.

For purposes of this invention, a dose description of 10 mg when referring to (R)-6-(2-(ethyl(4-(2-(ethylamino)ethyl)benzyl)amino)-4-methoxyphenyl)-5,6,7,8-tetrahydronaphthalen-2-ol dihydrochloride means about 10 mg of the entire weight of the compound as its salt (e.g., an acid addition salt, dihydrochloride salt or hydrogen chloride salt) such as its dihydrochloride salt. Small variations about the 10 mg should be considered to fall within the 10 mg description of this invention. For example, differences in weighing, humidity, small impurities of the synthesis, etc means that a dose range from 9 mg to 11 mg will be considered equal to 10 mg for purpose of the description in this invention.

For purposes of this invention, a dose description of 1 mg, 2.5 mg or 5 mg when referring to (R)-6-(2-(ethyl(4-(2-(ethylamino)ethyl)benzyl)amino)-4-methoxyphenyl)-5,6,7,8-tetrahydronaphthalen-2-ol dihydrochloride means about 1 mg, 2.5 mg or 5 mg of the entire weight of the compound as its salt (e.g., an acid addition salt, dihydrochloride salt or hydrogen chloride salt), such as its dihydrochloride salt. Small variations about the 1 mg, 2.5 mg or 5 mg should be considered to fall within the weight description of this invention. For example, differences in weighing, humidity, small impurities of the synthesis, etc means that a dose range from 0.9 mg to 1.1 mg will be considered equal to 1 mg for purpose of the description in this invention or 2.2 mg to 2.8 mg will be considered equal to 2.5 mg for purpose of the description in this invention, or 4.4 mg to 5.6 mg will be considered equal to 5 mg for purpose of the description in this invention.

For purposes of this invention, the compound (R)-6-(2-(ethyl(4-(2-(ethylamino)ethyl)benzyl)amino)-4-methoxyphenyl)-5,6,7,8-tetrahydronaphthalen-2-ol dihydrochloride may vary to a certain degree with regard to the amount of the (S)-enantiomer that may be present in the drug product. For example, when (R)-6-(2-(ethyl(4-(2-(ethylamino)ethyl)benzyl)amino)-4-methoxyphenyl)-5,6,7,8-tetrahydronaphthalen-2-ol dihydrochloride is referred to, it should be understood that it generally will contain at least 95% of the R-enantiomer and up to 5% of the S-enantiomer. For purposes of calculating the desired dosaging amount, the S-enantiomer will be included in the total weight of the drug provided it does not exceed the 5% preferred limit set in this definition. However, if the drug substance is dosed having >5% of the (S)-enantiomer, then the (S)-enantiomer will be subtracted from the total weight of the drug substance for purposes of dosaging calculations.

For purposes of this invention, the phrase "essentially dissolved in the stomach" means that after oral administration of a dosage form of this invention or a method of this invention, the compound (R)-6-(2-(ethyl(4-(2-(ethylamino)ethyl)benzyl)amino)-4-methoxyphenyl)-5,6,7,8-tetrahydronaphthalen-2-ol is more than 50% dissolved in the stomach prior to being released into the duodenum. In certain embodiments of this invention, the phrase "essentially dissolved in the stomach" means that after oral administration of a dosage form of this invention or a method of this invention, the compound (R)-6-(2-(ethyl(4-(2-(ethylamino)ethyl)benzyl)amino)-4-methoxyphenyl)-5,6,7,8-tetrahydronaphthalen-2-ol is more than 70% dissolved in the stomach prior to being released into the duodenum. In certain embodiments of this invention, the phrase "essentially dissolved in the stomach" means that after oral administration of a dosage form of this invention or a method of this invention, the compound (R)-6-(2-(ethyl(4-(2-(ethylamino)ethyl)benzyl)amino)-4-methoxyphenyl)-5,6,7,8-tetrahydronaphthalen-2-ol is more than 90% dissolved in the stomach prior to being released into the duodenum. The dissolution of (R)-6-(2-(ethyl(4-(2-(ethylamino)ethyl)benzyl)amino)-4-methoxyphenyl)-5,6,7,8-tetrahydronaphthalen-2-ol in the stomach can be affected by different parameters, particularly those related to the excipients that the compound is co-formulated with and especially to whether the dosage formulation form is coated with a material that prevents dissolution of the coating material in the acid environment of the stomach. In some embodiments of this invention, it should be noted that the dosage form is not coated with an acid resistant coating. For purposes of this invention, an acid resistant coating refers to a coating on a tablet, granule, tablet, capsule or any other particle that contains (R)-6-(2-(ethyl(4-(2-(ethylamino)ethyl)benzyl)amino)-4-methoxyphenyl)-5,6,7,8-tetrahydronaphthalen-2-ol within it. An acid resistant material means that the coating is resistant to pH's of up to about 5.5. Acid resistant coating materials are well known by those of ordinary skill in the art and include materials such as polymeric acids such as methacrylic acid polymers, and the like. Acid resistant materials also include such materials as waxes, shellacs, fatty acids, polymeric acids, plant fibers and the like.

In some embodiments of this invention, it may be preferable to provide the drug in a form that avoids or largely avoids exposure of the drug substance in the person's stomach being treated. For example, a patient suffering from gastritis or some other form of irritation in the stomach may prefer to take a dosage formulation that largely or completely bypasses the direct exposure of the drug to the stomach lining. In this regard, a coating may be added to the drug dosage form such as an enteric coating that is stable in the acidic pH in the stomach but is more readily dissolved in the less acidic environment of the small intestine. Acid resistant materials also include such materials as waxes, shellacs, fatty acids, polymeric acids, plant fibers and the like.

For purposes of this invention, the term "vasomotor disturbances" refers to the constellation of central nervous system disturbances associated with the peri- and postmenopausal period. In particular, vasomotor disturbances includes hot flashes and/or hot flushes that are severe, moderate or mild. Vasomotor disturbances may also include inappropriate sweating and/or sweating at night. Vasomotor disturbances is sometimes referred to in the art as "vasomotor symptoms" associated with the peri- or postmenopause periods.

For purposes of this invention, a "perimenopausal woman" is a woman who is transitioning into menopause. The perimenopausal period is not strictly defined but rather is understood by one of skill in the medical arts to include women whose estrogen levels have begun to fluctuate unevenly often leading to irregular menstrual cycles. The perimenopausal period typically begins several years before true menopause and includes up to one year after the woman's final menstrual period. From a functional perspective with regard to treating a perimenopausal woman with the compositions and methods of this invention, the perimenopausal period is most easily identified by the symptoms associated with it. If a woman is still having her menstrual periods or has within one year had a menstrual period but yet she is at least 30 years of age and more likely at least 40 years of age and is experiencing hot flashes/flushes, night sweats, unusual anxiety, depression and/or mood swings then she can be considered as a perimenopausal woman for who this invention can be of value.

For purposes of this invention description, the term "postmenopausal woman" refers to any woman who has is at least 40 years of age and is naturally amenorrheic for a period of at least one year or has elevated FSH levels (>25 mIU in some embodiments, >30 mIU in some embodiments and >50 mIU in other embodiments). In some embodiments of this invention, the term "postmenopausal woman" refers to women who are amenorrheic through surgical removal of the ovaries. In yet other aspects of this invention, the term "postmenopausal woman" refers to women who are amenorrheic through treatment with an agent that causes suppression of ovarian function such as leutinizing hormone agonists (eg leuprolide), antagonists or gonadotropin hormone releasing hormone antagonists such (eg ganirelix).

EXAMPLE

A phase 2a study was undertaken to assess the effect of (R)-6-(2-(ethyl(4-(2-(ethylamino)ethyl)benzyl)amino)-4-methoxyphenyl)-5,6,7,8-tetrahydronaphthalen-2-ol dihydrochloride (referred to as "drug" in tables below) to alleviate hot flashes in postmenopausal women. The study design and objectives are detailed below.

Study Objectives

The overall objectives of the study were to assess the clinical safety and efficacy of (R)-6-(2-(ethyl(4-(2-(ethylamino)ethyl)benzyl)amino)-4-methoxyphenyl)-5,6,7,8-tetrahydronaphthalen-2-ol dihydrochloride in postmenopausal women with frequent, moderate to severe vasomotor symptoms. Changes in frequency and severity of symptoms were assessed. Data was evaluated to analyze the effect of increasing doses of (R)-6-(2-(ethyl(4-(2-(ethylamino)ethyl)benzyl)amino)-4-methoxyphenyl)-5,6,7,8-tetrahydronaphthalen-2-ol dihydrochloride on overall efficacy.

The specific objectives of this study are to:
Monitor the effects of 28-days of treatment with (R)-6-(2-(ethyl(4-(2-(ethylamino)ethyl)benzyl)amino)-4-methoxyphenyl)-5,6,7,8-tetrahydronaphthalen-2-ol dihydrochloride on frequency and severity of hot flashes in postmenopausal women with frequent, moderate to severe vasomotor symptoms.
Monitor the safety and tolerability of 28-days of dosing with (R)-6-(2-(ethyl(4-(2-(ethylamino)ethyl)benzyl)amino)-4-methoxyphenyl)-5,6,7,8-tetrahydronaphthalen-2-ol dihydrochloride in postmenopausal women with frequent, moderate to severe vasomotor symptoms.

Study Population

Planned Inclusion Criteria

Postmenopausal women from 40 to 75 years of age (inclusive) who meet the study entry criteria and have provided written informed consent will be eligible for the study. The women will be established to be postmenopausal on the basis of menstrual history (one year of amenorrhea) and/or serum FSH levels. Women with documented surgical menopause who meet the study entry criteria will also be eligible 6 months after surgery. The principal entry criterion is a documented history of moderate to severe hot flashes with an event frequency of 7 per day or 50 per week. All patients are to be in good general health as determined by medical history, physical examination (including pelvic examination and Pap test) and clinical laboratory testing. Pelvic ultrasound should also demonstrate no clinically significant abnormality. Breast health should be confirmed by mammogram in the past 6 months or at screening. Body Mass Index (BMI) of 18-30 kg/m² (inclusive). The resting 12-lead ECG obtained during screening should have no clinically significant abnormality and a QTc (Bazett's correction) of ≤450 msec.

Planned Exclusion Criteria

Patients reporting recent use (within 6 months of enrollment) of estrogens, SERMs, or other estrogen preparations might be excluded, as will those with recent (within 3 months of enrollment) use of any medication known to reduce or enhance vasomotor symptoms. Women with a history of thrombosis or blood clotting disorders, chronic medical or psychiatric illness, and breast, uterine or other cancer might be excluded. Patients with known substance abuse problems will also be excluded and patients who have received an investigational drug product in the past 12 months might be excluded.

Patients must have understood and agreed to comply with all study requirements and had signed the written Informed Consent Form (ICF).

Study Design and Methodology

Number of Patients

A total of 100 patients are planned to be enrolled in the study.

Design

This is a randomized, placebo-controlled, double-blind, parallel-group, Phase 2, multi-center, dose-finding study to evaluate the effects of (R)-6-(2-(ethyl(4-(2-(ethylamino) ethyl)benzyl)amino)-4-methoxyphenyl)-5,6,7,8-tetrahydronaphthalen-2-ol dihydrochloride in the treatment of vasomotor symptoms in postmenopausal women.

A total of 100 eligible patients will be randomized to receive one of 5 blinded treatment regimens. (R)-6-(2-(ethyl (4-(2-(ethylamino)ethyl)benzyl)amino)-4-methoxyphenyl)-5,6,7,8-tetrahydronaphthalen-2-ol dihydrochloride at doses 0, 10, 25, 50 or 100 mg will be dosed for 28-days. The dosages of study medications and the number of patients randomized to each treatment regimen are shown in Table 1.

TABLE 1

| Treatment Regimen | Study Medication | Daily Dose (PO) | Number of Patients |
| --- | --- | --- | --- |
| 1 | drug | 10 mg | 20 |
| 2 | drug | 25 mg | 20 |
| 3 | drug | 50 mg | 20 |

TABLE 1-continued

| Treatment Regimen | Study Medication | Daily Dose (PO) | Number of Patients |
| --- | --- | --- | --- |
| 4 | drug | 100 mg | 20 |
| 5 | Placebo | — | 20 |
| | | Total | 100 |

Study Visits

The study periods and number of clinic visits are summarized in Table 2.

TABLE 2

| Study Period | Duration of Study Period | Scheduled Visits (#) |
| --- | --- | --- |
| Screening | ≤2 weeks | 2 |
| Treatment | 4 weeks | 4 |
| Follow-up | 1 month | 1 |
| Total | ~10 Weeks | 7 |

Planned Procedures and Assessments

Efficacy

Patients will document in real time hot flash frequency and severity according to a predetermined scale, in the provided electronic or paper Study Diary. Study Diary entries of hot flash frequency and severity and associated symptoms will be reviewed at each study visit. Serum markers of estrogen effect will be measured at specific study visits while on treatment.

Safety

Safety evaluations include physical examinations, vital signs, 12-lead ECG, clinical laboratory tests, and adverse events. Study specific algorithms for management of vaginal bleeding and clinically significant breast tenderness have been included.

Safety laboratory assessments will be performed at specific study visits during the treatment period and the final visit. All patients will be monitored for cardiac safety (QTc interval assessment) at specific study visits using a standardized 12-lead ECG.

Endpoints and Data Analysis

The efficacy endpoints assessed are:
Change in frequency of hot flashes over time
Change in severity of hot flashes over time;
Change in composite score of hot flashes over time (frequency×severity)

The safety data includes the incidence and severity of adverse events by dose and cumulative dose, and the pathological changes in hematology, chemistry and urinalysis data. Changes in physical examination, vital signs, ECG and clinical laboratory tests will be summarized using descriptive statistics. Shift frequencies will be summarized for clinical laboratory tests.

Treatment groups will be assessed for uniformity at baseline (baseline characteristics, medical history, physical examination, vital signs, and ECG).

Treatments Administered (R)-6-(2-(ethyl(4-(2-(ethylamino)ethyl)benzyl)amino)-4-methoxyphenyl)-5,6,7,8-tetrahydronaphthalen-2-ol dihydrochloride was provided by sponsor in capsule form for oral administration. All doses (0, 10, 25, 50 and 100 mg) were provided as identical presentations. Each patient was provided with 2 containers of 28-capsules each at the start of treatment and took one capsule from each container every day for 28-days. Placebo contained the same excipients as active medication, but without (R)-6-(2-(ethyl(4-(2-(ethylamino)ethyl)benzyl)amino)-4-methoxyphenyl)-5,6,7,8-tetrahydronaphthalen-2-ol dihydrochloride. The patients were instructed to take the capsules orally in the fasted state (morning).

Capsule Formulations

The capsules containing (R)-6-(2-(ethyl(4-(2-(ethylamino)ethyl)benzyl)amino)-4-methoxyphenyl)-5,6,7,8-tetrahydronaphthalen-2-ol dihydrochloride were prepared in dosage strengths of 0 mg, 10 mg, 25 mg and 50 mg. The composition of the capsules is shown in Table 3.

TABLE 3

| Strength of capsule** | Content (drug) | Prosolv ®* | Total weight |
|---|---|---|---|
| 0 mg | 0 mg | 69.1 mg | 69.1 mg |
| 10 mg | 10.3 mg | 58.8 mg | 69.1 mg |
| 25 mg | 25.8 mg | 43.3 mg | 69.1 mg |
| 50 mg | 51.5 mg | 17.6 mg | 69.1 mg |

*Silicified microcrystalline cellulose, as a combination of 98% microcrystalline cellulose (MCC) and 2% colloidal silicon dioxide (CSD). SMCC 50 (JRS Pharma; Holzmühle 1 D-73494 Rosenberg (Germany); 2981 Route 22, Suite 1 Patterson, NY 12563-2359 (USA).
**Capsules used were Capsugel (100 Route 206 North/Pfizer Way, Peapack, NJ 07977 USA) Coni-Snap ® gelatin capsules, size 4, white opaque.

A slight excess of (R)-6-(2-(ethyl(4-(2-(ethylamino)ethyl)benzyl)amino)-4-methoxyphenyl)-5,6,7,8-tetrahydronaphthalen-2-ol dihydrochloride was used in order to compensate for residual impurities and moisture in the drug product. Each patient self-administered two capsules to which they were blinded with regard to the capsule contents. The placebo group received 2-0 mg capsules; the 10 mg group received 1-10 mg capsule and 1-0 mg capsule; the 25 mg group received 1-25 mg capsule and 1-0 mg capsule; the 50 mg group received 1-50 mg capsule and 1-0 mg capsule; and the 100 mg group received 2-50 mg capsules.

Capsules containing 1, 2.5 and 5 mg of drug can be similarly prepared.

Planned Duration of Patient Participation

The maximum duration of study participation for an individual patient is approximately 10-weeks (72 days) from the initial Screening visit to the completion of final study evaluations. Patients will complete screening procedures during the Screening Period within 14 days prior to the first dose of study medication. After completion of the Screening Period, patients will be randomized if they meet the entrance criteria and will receive the first dose of study medication on Day 1 of the Treatment Period. The Treatment Period will be 28 days in duration and will involve daily oral self-administration of (R)-6-(2-(ethyl(4-(2-(ethylamino)ethyl)benzyl)amino)-4-methoxyphenyl)-5,6,7,8-tetrahydronaphthalen-2-ol dihydrochloride or its Placebo and documentation of hot flashes/symptoms using a Study Diary. After completion of 28 days of dosing, patients will return to the clinic for the End-of-Treatment Visit (Day 29) and enter the Follow-up Period of 30 days. The end of patient participation will be at the End-of-Study Visit, scheduled at the end of the Follow-up Period.

Study Results

Analyzed

A total of 136 patients were screened of which 36 (26.5%) were screen failures; therefore, 100 patients were enrolled and randomized in the study. Of the 100 patients enrolled, 100 were included in the Safety/Intent-to-Treat (ITT) population and 81 were included in the Per-Protocol Population (PP).

Duration of Treatment

The treatment period duration was 4 weeks. The maximum duration of study participation for an individual patient was approximately 10 weeks (72 days) from the initial Screening visit to the completion of final study evaluations.

Efficacy

Efficacy was assessed by evaluating change including baseline and percent change from baseline for the following primary endpoints:
Frequency of hot flashes
Severity of hot flashes
Composite score of hot flashes over time (frequency× severity)
drug levels Statistical Methods The following analysis populations were analyzed in this study: Safety population (Safety/Intent-to-treat [ITT]), defined as all patients who received one or more doses of study drug, and Per-Protocol Population (PP) defined as all patients of the ITT Population who met all entrance criteria or had a waiver of unmet criterion, had not used any prohibited concomitant medications, met study drug compliance of 90%, provided acceptably complete (25 days of full data) diary information, and met assessment and visit compliance at baseline and End-of-Treatment Visits. All efficacy endpoints were to be analyzed for the ITT and PP populations, with the exception of the drug levels (analyzed for the ITT population only). Safety endpoints were to be analyzed for the Safety/ITT population.

Continuous, quantitative variable summaries included the number of patients (N) (with non missing values), mean, standard deviation, median, minimum, maximum, and 95% confidence interval. Categorical, qualitative variable summaries included the frequency and percentage of patients who were in the particular category. In general, the denominator for the percentage calculation was to be based upon the total number of patients in the study population for the treatment groups at the specific timepoint, unless otherwise specified. Descriptive summaries were to be presented for the number and percentage of patients in each study population (overall and by center), disposition of patients (including number of patients screened, screen failure patients, and patients randomized, completed and withdrawn), and study withdrawals by reason of withdrawal. Summaries of demographics and baseline characteristics were to include the following: age, race, height, weight, BMI, medical history (time since last menses and number of months of hot flash history), hot flash history (moderate, severe, and moderate and severe), and concomitant medication at baseline, Baseline physical examination (abnormal and normal), vital signs (systolic and diastolic blood pressure, pulse rate, temperature, respiratory rate), and 12-lead ECG (abnormal and normal). Summaries of AEs, clinical laboratory investigations (chemistries, hematology, coagulation, serum estradiol, and urinalysis), vital signs (blood pressure, pulse rate, respiratory rate, and body temperature), physical examinations, ECG investigations, and pelvic ultrasound were to be provided. Adverse events of vaginal bleeding and breast tenderness (and related breast events) were to be tabulated separately.

Changes in the efficacy endpoints of frequency, severity, and composite score of hot flashes over time; associated hot flash symptoms (palpitations, insomnia, joint aches, and headaches), PD markers of estrogen effect (FSH, LH, and lipid profile), drug levels, and MRS were to be summarized using descriptive statistics. Frequency, severity, and composite score of hot flashes over time were to be analyzed using repeated measures analysis of variance (ANOVA) with factors for treatment (treatment groups), time (study day) and their interaction. A linear trend test for treatment groups (placebo, and 10, 25, 50, 100 mg doses of drug) and for study day as well as any potential interaction between the two was to be included as part of the analyses by including both dose and time as continuous variables in the ANOVA model. Pair-wise comparisons of change from baseline were to be tested between the placebo group and each drug dose group for each timepoint; the mean difference together with a 95% confidence interval of the difference was to be presented for placebo compared with each active treatment group. Nominal p-values at Week 4 were to be presented. In addition, graphical presentations of mean (±standard error of the mean) and percent group responses over time together with repeated measures ANOVA to assess potential trend in responses over time in each dose group were to be presented. For the associated vasomotor symptoms (palpitations, insomnia, joint aches, and headaches collected in the patient diaries), patient and event frequencies were to be summarized by treatment week and treatment group.

Additional exploratory, post-hoc analyses were to be performed as appropriate to complement the overall understanding of study results.

Descriptive summaries of actual (absolute) values and changes from baseline values by study visit were to be presented for hematology, chemistry, coagulation, serum estradiol, and urinalysis by treatment for the safety population. Additionally, for each laboratory parameter, shifts in assessments from baseline to End-of Treatment Visit and End-of-Study Visit were to be presented (shift tables).

Results

Pharmacokinetic Evaluation

TABLE 4

| | Mean Trough Level of Drug (ng/mL) (ITT) | | | | |
|---|---|---|---|---|---|
| Visit | Placebo | 10 mg (SD) | 25 mg (SD) | 50 mg (SD) | 100 mg (SD) |
| Day 8 | 0.00 | 0.45 (0.34) | 1.33 (0.52) | 3.11 (1.66) | 6.91 (4.39) |
| Day 15 | 0.00 | 0.49 (0.37) | 1.49 (0.71) | 3.39 (2.01) | 6.66 (4.60) |
| Day 29 | 0.00 | 0.34 (0.26) | 1.18 (0.73) | 3.23 (2.41) | 6.03 (4.46) |

SD = standard deviation in ng/mL

TABLE 5

| | Peak Level of drug (ng/mL) (ITT) | | | | |
|---|---|---|---|---|---|
| Visit | Placebo | 10 mg (SD) | 25 mg (SD) | 50 mg (SD) | 100 mg (SD) |
| Day 1 | 0.00 | 0.56 (0.34) | 1.41 (0.63) | 2.83 (1.72) | 8.39 (4.04) |
| Day 8 | 0.00 | 0.92 (0.52) | 2.53 (0.74) | 6.36 (2.58) | 15.47 (7.14) |
| Day 15 | 0.00 | 0.92 (0.69) | 2.97 (1.09) | 6.22 (3.46) | 12.76 (5.28) |

SD = standard deviation in ng/mL

Values for ranges of steady state trough levels and steady state Cmax can be derived from Tables 4 and 5. Steady state values are the values listed for days 8 and 15. The ranges were derived from the mean number listed in the table plus or minus one standard deviation (the number in parenthesis after each mean value). For example a steady state trough level ranging from 0.11 ng/mL to 0.79 ng/mL is derived from Table 4 by taking the trough level for 10 mg, 0.45 ng/mL, adding 0.34 to get the upper value of 0.79 and subtracting 0.34 to get the lover value of 0.11. Other ranges for steady state trough levels and ranges for Cmax can be similarly derived from the data in Tables 4 and 5.

Hot Flash Frequency

Moderate and Severe Hot Flash Frequency

The total number of hot flashes rated as moderate and severe were reported as a weekly mean for each treatment group. As can be seen in Table 6, the 10 mg treatment group demonstrated the best treatment effect.

TABLE 6

| | | Weekly Mean Frequency of Moderate and Severe Hot Flash Numbers (ITT) | | | | | |
|---|---|---|---|---|---|---|---|
| | | Treatment Group | | | | | |
| Timepoint | Statistic | Placebo N = 19 | 10 mg N = 22 | 25 mg N = 20 | 50 mg N = 21 | 100 mg N = 18 | Total N = 100 |
| Baseline | N | 18 | 22 | 19 | 21 | 17 | 97 |
| | Mean (SD) | 61.3 (12.84) | 63.1 (14.23) | 65.9 (44.30) | 71.9 (36.92) | 58.5 (12.67) | 64.4 (27.81) |
| Week 1 | N | 18 | 22 | 17 | 20 | 17 | 94 |
| | Mean (SD) | 41.2 (24.39) | 30.4 (18.92) | 57.7 (50.49) | 41.7 (23.79) | 41.9 (24.23) | 41.9 (30.37) |
| Week 2 | N | 17 | 20 | 17 | 18 | 17 | 89 |
| | Mean (SD) | 36.6 (25.48) | 18.5 (13.34) | 42.3 (49.73) | 32.8 (25.52) | 35.6 (28.06) | 32.7 (30.72) |

TABLE 6-continued

Weekly Mean Frequency of Moderate and Severe Hot Flash Numbers (ITT)

| | | Treatment Group | | | | | |
|---|---|---|---|---|---|---|---|
| Timepoint | Statistic | Placebo N = 19 | 10 mg N = 22 | 25 mg N = 20 | 50 mg N = 21 | 100 mg N = 18 | Total N = 100 |
| Week 3 | N | 17 | 20 | 17 | 18 | 16 | 88 |
| | Mean (SD) | 33.6 (24.80) | 14.5 (11.92) | 43.3 (57.15) | 29.6 (25.09) | 24.5 (24.06) | 28.7 (32.62) |
| Week 4 | N | 16 | 20 | 17 | 18 | 15 | 86 |
| | Mean (SD) | 29.5 (24.53) | 13.4 (11.54) | 37.4 (54.76) | 29.4 (26.53) | 18.6 (19.16) | 25.4 (31.29) |

Abbreviations:
(SD) = standard deviation

The graphical representation of the data from table 6 is shown in FIG. 1. The 10 mg group demonstrated the greatest reduction in hot flashes at each weekly time point.

Total Hot Flash Frequency

The total number of hot flashes rated as mild, moderate and severe (all hot flashes) were reported as a weekly mean for each treatment group. As can be seen in Table 7, the 10 mg treatment group demonstrated the greatest reduction in hot flashes at each weekly time point and once again demonstrates the best treatment effect.

TABLE 7

Weekly Mean Frequency of Mild, Moderate and Severe Hot Flash Numbers (ITT)

| | | Treatment Group | | | | | |
|---|---|---|---|---|---|---|---|
| Timepoint | Statistic | Placebo N = 19 | 10 mg N = 22 | 25 mg N = 20 | 50 mg N = 21 | 100 mg N = 18 | Total N = 100 |
| Baseline | N | 18 | 22 | 19 | 21 | 17 | 97 |
| | Mean (SD) | 65.2 (13.29) | 66.0 (13.89) | 75.8 (46.46) | 76.0 (36.96) | 63.6 (13.23) | 69.5 (28.66) |
| Week 1 | N | 18 | 22 | 17 | 20 | 17 | 94 |
| | Mean (SD) | 46.7 (23.56) | 36.0 (18.97) | 64.4 (48.88) | 54.0 (27.15) | 48.6 (23.32) | 49.3 (30.45) |
| Week 2 | N | 17 | 20 | 17 | 18 | 17 | 89 |
| | Mean (SD) | 40.1 (23.88) | 27.2 (15.16) | 48.0 (48.80) | 45.8 (25.16) | 41.6 (27.37) | 40.1 (30.03) |
| Week 3 | N | 17 | 20 | 17 | 18 | 16 | 88 |
| | Mean (SD) | 38.7 (25.25) | 21.2 (12.99) | 46.6 (56.27) | 40.5 (22.37) | 29.4 (23.91) | 34.9 (31.91) |
| Week 4 | N | 16 | 20 | 17 | 18 | 15 | 86 |
| | Mean (SD) | 34.9 (30.84) | 19.1 (12.95) | 42.4 (53.18) | 37.9 (23.45) | 23.1 (19.45) | 31.3 (31.52) |

Abbreviations:
(SD) = standard deviation

Figure 2:
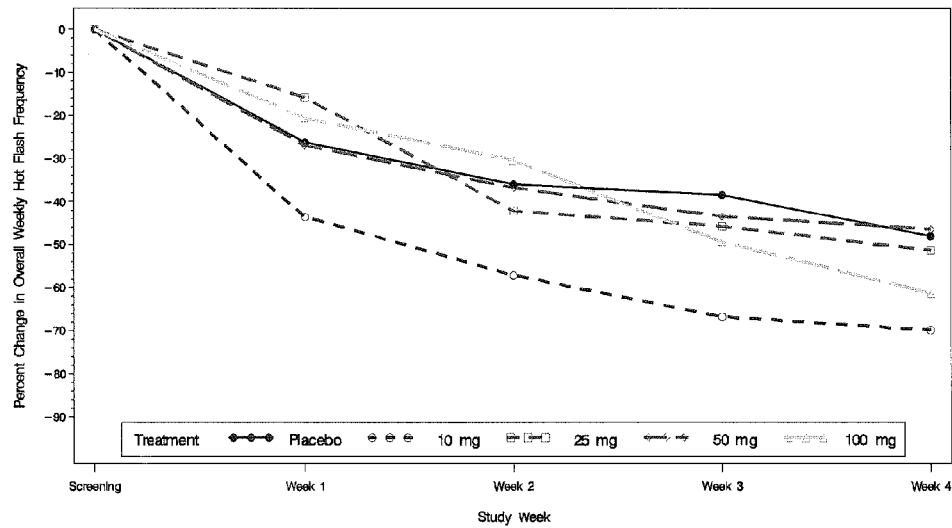
FIG. 2 is a graph showing the reduction in mean weekly frequency of all hot flashes (ITT).

The graphical representation of the data from Table 7 is shown in FIG. 2.

Hot Flash Severity

Figure 3:
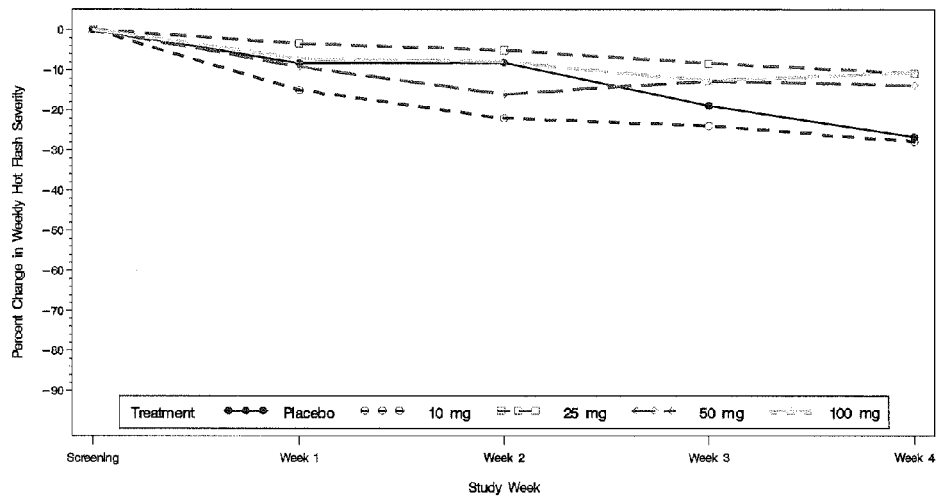
FIG. 3 is a graph showing reduction in mean severity of all hot flashes (ITT).

Hot flashes were also scored according to their severity with a mild hot flash scored a "1", a moderate hot flash scored a "2" and a severe hot flash scored a "3". A mean hot flash severity can be derived by taking the sum of the total obtained by multiplying the total frequency of hot flashes in each group (mild, moderate or severe) by the severity assigned to that type of hot flash (1, 2 or 3, respectively) and then dividing the total by the frequency of all hot flashes. This gives the mean severity and is averaged over a week period and presented in Table 8. A graph of the data from Table 8 is shown in FIG. 3. The 10 mg dose had the greatest reduction in severity of hot flashes at all time points.

TABLE 8

Mean Severity Scores by Week (ITT)

| | | Treatment Group | | | | | |
|---|---|---|---|---|---|---|---|
| Timepoint | Statistic | Placebo N = 19 | 10 mg N = 22 | 25 mg N = 20 | 50 mg N = 21 | 100 mg N = 18 | Total N = 100 |
| Baseline | N | 18 | 22 | 19 | 21 | 17 | 97 |
| | Mean (SD) | 2.36 (0.430) | 2.37 (0.347) | 2.26 (0.348) | 2.14 (0.313) | 2.21 (0.330) | 2.27 (0.359) |
| Week 1 | N | 18 | 22 | 17 | 20 | 17 | 94 |
| | Mean (SD) | 2.12 (0.397) | 1.99 (0.460) | 2.12 (0.392) | 1.92 (0.402) | 2.04 (0.334) | 2.03 (0.401) |

TABLE 8-continued

Mean Severity Scores by Week (ITT)

| | | Treatment Group | | | | | |
|---|---|---|---|---|---|---|---|
| Timepoint | Statistic | Placebo N = 19 | 10 mg N = 22 | 25 mg N = 20 | 50 mg N = 21 | 100 mg N = 18 | Total N = 100 |
| Week 2 | N | 17 | 20 | 17 | 17 | 17 | 88 |
| | Mean (SD) | 2.11 (0.446) | 1.80 (0.514) | 2.09 (0.447) | 1.88 (0.535) | 2.01 (0.406) | 1.97 (0.478) |
| Week 3 | N | 16 | 19 | 16 | 18 | 16 | 85 |
| | Mean (SD) | 2.00 (0.482) | 1.84 (0.570) | 2.14 (0.408) | 1.86 (0.544) | 1.88 (0.473) | 1.94 (0.503) |
| Week 4 | N | 14 | 18 | 16 | 18 | 15 | 81 |
| | Mean (SD) | 1.94 (0.504) | 1.86 (0.562) | 2.06 (0.404) | 1.83 (0.568) | 1.89 (0.484) | 1.91 (0.505) |

Abbreviations:
(SD) = standard deviation

Hot Flash Composite Score

Figure 4:
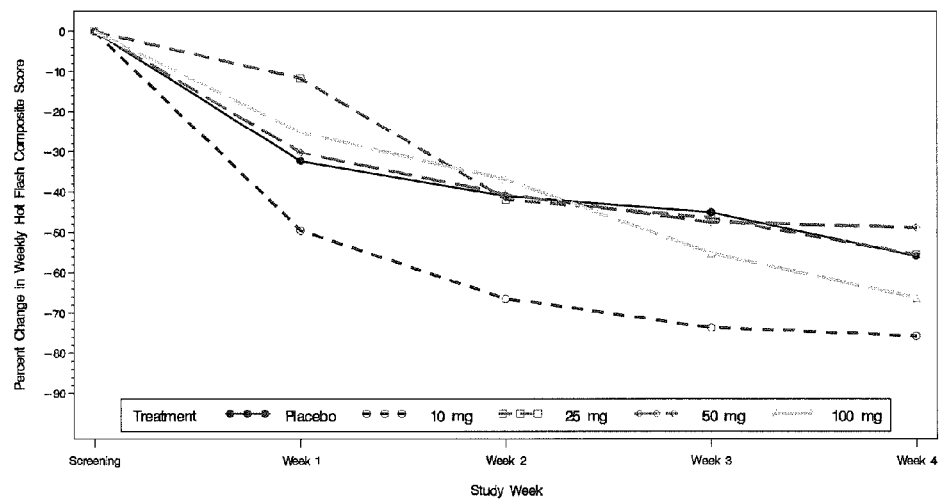
FIG. 4 is a graph showing the reduction in weekly composite scores.

A composite score that takes into account both the total frequency and the mean severity was calculated by multiplying together that patient's mean weekly severity with that patient's total hot flash frequency to give the composite score. The composite index is a helpful measure of the overall alleviation of hot flash burden. Table 9 lists the composite scores for the treatment groups. FIG. 4 is a graphical representation of the data in Table 9. The composite score indicates that the 10 mg group had the greatest composite score reduction at each weekly timepoint.

TABLE 9

Composite Scores by Week (ITT)

| | | Treatment Group | | | | | |
|---|---|---|---|---|---|---|---|
| Timepoint | Statistic | Placebo N = 19 | 10 mg N = 22 | 25 mg N = 20 | 50 mg N = 21 | 100 mg N = 18 | Total N = 100 |
| Baseline | N | 18 | 22 | 19 | 21 | 17 | 97 |
| | Mean (SD) | 155.17 (47.09) | 156.45 (38.91) | 165.47 (119.10) | 162.19 (76.44) | 140.35 (36.82) | 156.40 (69.97) |
| Week 1 | N | 18 | 22 | 17 | 20 | 17 | 94 |
| | Mean (SD) | 98.44 (54.65) | 73.68 (41.67) | 142.71 (125.55) | 104.35 (55.52) | 104.35 (68.35) | 102.98 (74.70) |
| Week 2 | N | 17 | 20 | 17 | 18 | 17 | 89 |
| | Mean (SD) | 86.24 (57.05) | 47.75 (24.95) | 102.82 (118.57) | 87.78 (54.61) | 87.18 (74.31) | 81.25 (72.30) |
| Week 3 | N | 17 | 20 | 17 | 18 | 16 | 88 |
| | Mean (SD) | 80.29 (55.48) | 37.15 (21.96) | 102.59 (139.75) | 77.67 (51.87) | 59.75 (62.00) | 70.52 (77.19) |
| Week 4 | N | 16 | 20 | 17 | 18 | 15 | 86 |
| | Mean (SD) | 69.31 (57.98) | 34.35 (23.48) | 89.59 (134.32) | 75.06 (55.82) | 43.67 (40.32) | 61.92 (73.76) |

Abbreviations:
(SD) = standard deviation

Taken in sum, the data presented herein demonstrate the unexpected and surprisingly consistent reduction on hot flash incidence and severity of the lowest dose tested (10 mg) compared to placebo and three higher doses. This discovery is not only unexpected and surprising but potentially beneficial as well. In general, the ability to use a lower dose suggests a lower cost of goods as well as decreased likelihood of side effects or off target effects that tend to increase as dosage of any drug is increased.

When the effect of the compound of formula I at 10 mg is analyzed by concentration of drug in the plasma and compared to its efficacy, it was observed that the lower concentration cohort experienced similar efficacy as the higher concentration cohort. For example, in one analysis, a cohort with a 2 hour postdose plasma concentration range of between 0.43 ng/mL to 0.53 ng/mL of the compound of formula I had a similar efficacy in hot flush frequency reduction (−75%) as the higher concentration cohort having a range of 0.66 ng/mL to 1.34 ng/mL (−77%). This indicates that lower dosages of the compound of formula I such as 5 mg, 2.5 mg or 1 mg can be effective.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A unit dosage form suitable for once daily administration to a human subject in need thereof comprising 0.9 mg to 1.1 mg, 2.2 mg to 2.8 mg, 4.4 mg to 5.6 mg, or 9 mg to 11 mg of the compound of formula I as its dihydrochloride salt

21

Formula I

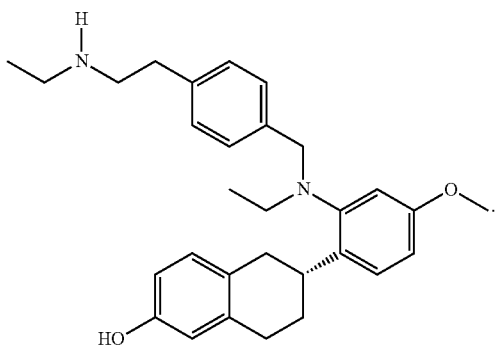

2. The unit dosage form according to claim 1, further comprising one or more pharmaceutically acceptable excipients.

3. The unit dosage form according to claim 2, wherein the unit dosage form is a tablet or capsule suitable for oral administration.

4. A unit dosage form comprising 0.9 mg to 1.1 mg, 2.2 mg to 2.8 mg, 4.4 mg to 5.6 mg, or 9 mg to 11 mg of the compound of formula I or a salt thereof Formula I

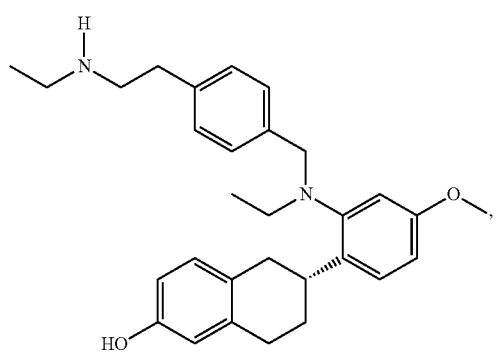

wherein following oral administration the unit dosage form, is more than 50% dissolved in the stomach prior to being released into the small intestines.

5. The unit dosage form according to claim 4, wherein the unit dosage form is not coated with an acid resistant coating.

6. A method of treating vasomotor disturbances in a peri-menopausal or postmenopausal woman in need thereof comprising administering to the woman a composition comprising a compound of formula I or a salt thereof Formula I

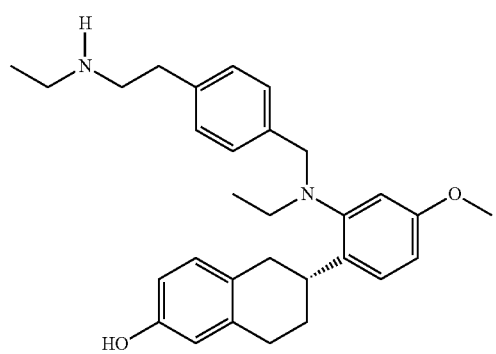

22 at a daily total dosage of the compound of formula I or a salt thereof at a range from 0.9 mg to 1.1 mg, 2.2 mg to 2.8 mg, 4.4 mg to 5.6 mg, or 9 mg to 11 mg.

7. The method according to claim 6, wherein the composition is administered orally, once-daily.

8. The method according to claim 7, wherein the composition is a tablet or capsule suitable for oral administration.

9. The method according to claim 8, wherein the composition is more than 50% dissolved in the stomach prior to being released into the small intestines.

10. The method according to claim 9, wherein the composition is not coated with an acid resistant coating.

11. A method of treating vasomotor disturbances in a peri-menopausal or postmenopausal woman in need thereof comprising administering to the woman a compound of formula I or a salt thereof Formula I wherein the administration results in a steady state Cmax of from 0.40 ng/mL to 1.43 ng/mL.

12. The method of claim 11, wherein a steady state trough level of the compound of formula I ranging from 0.11 ng/mL to 0.79 ng/mL or ranging from 0.12 ng/mL to 0.86 ng/mL is achieved.

13. The method of claim 11, wherein the compound of formula I is in the form of a dihydrochloride salt.

14. The method of claim 13, wherein the compound of formula I or a salt thereof is orally administered once-daily.

15. The method of claim 14, wherein the compound is in a unit dosage form.

16. The method of claim 15, wherein the compound is administered as a capsule or tablet.

17. The method of claim 16, wherein the capsule or tablet is more than 50% dissolved in the stomach prior to being released into the small intestines.

18. The method according to claim 17, wherein the unit dosage form is not coated with an acid resistant coating.

19. A method of treating vasomotor disturbances in a peri-menopausal or postmenopausal woman in need thereof comprising administering to the woman a compound of formula I or a salt thereof

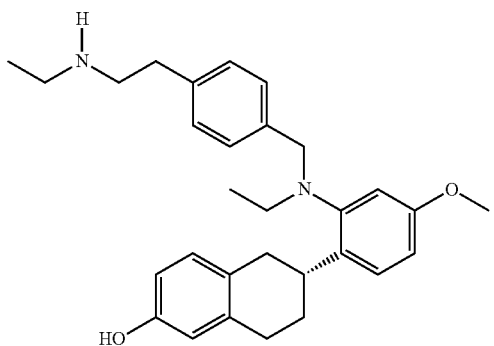

Formula I wherein the administration results in a steady state Cmax of from 0.22 ng/mL to 1.61 ng/mL.

20. The method of claim 19, wherein the compound of formula 1 is in its dihydrochloride salt form.

21. The method of claim 19, wherein a steady state trough level of the compound of formula I ranging from 0.11 ng/mL to 0.79 ng/mL or ranging from 0.12 ng/mL to 0.86 ng/mL is achieved.

22. The method of claim 19, wherein the compound of formula I is in the form of a dihydrochloride salt.

23. The method of claim 22, wherein the compound of formula I or a salt thereof is orally administered once-daily.

24. The method of claim 23, wherein the compound is in a unit dosage form.

25. The method of claim 24, wherein the unit dosage formulation is a capsule or tablet.

26. The method of claim 25, wherein the capsule or tablet is more than 50% dissolved in the stomach prior to being released into the small intestines.

27. The method according to claim 26, wherein the unit dosage form is not coated with an acid resistant coating.

28. The unit dosage form according to claim 1, wherein the unit dosage form comprises 1 mg, 2.5 mg, 5 mg, or 10 mg of the compound of Formula I or a salt thereof.

29. The unit dosage form according to claim 4, further comprising one or more pharmaceutically acceptable excipients.

30. The unit dosage form according to claim 29, wherein the unit dosage form is a tablet or capsule suitable for oral administration.

31. The unit dosage form according to claim 4, wherein the unit dosage form comprises 1 mg, 2.5 mg, 5 mg, or 10 mg of the compound of Formula I or a salt thereof.

32. The unit dosage form according to claim 4, wherein the unit dosage form comprises an acid addition salt of the compound of Formula I.

33. The unit dosage form according to claim 32, wherein the unit dosage form comprises a dihydrochloride salt of the compound of Formula I.

34. The method according to claim 6, wherein the daily total dosage of the compound of Formula I or a salt thereof is 1 mg, 2.5 mg, 5 mg, or 10 mg.

35. The method according to claim 6, wherein the composition comprises an acid addition salt of the compound of Formula I.

36. The method according to claim 35, wherein the composition comprises a dihydrochloride salt of the compound of Formula I.

* * * * *